United States Patent
Figge et al.

(10) Patent No.: US 9,732,364 B2
(45) Date of Patent: Aug. 15, 2017

(54) USE OF INDUCIBLE PROMOTERS IN THE PRODUCTION OF METHIONINE

(75) Inventors: Rainer Figge, Le Crest (FR); Perrine Vasseur, Martres sur Morges (FR)

(73) Assignee: EVONIK DEGUSSA GMBH, Essen (DE)

( * ) Notice: Subject to any disclaimer, the term of this patent is extended or adjusted under 35 U.S.C. 154(b) by 560 days.

(21) Appl. No.: 13/515,432

(22) PCT Filed: Dec. 13, 2010

(86) PCT No.: PCT/EP2010/069473
§ 371 (c)(1),
(2), (4) Date: Jun. 12, 2012

(87) PCT Pub. No.: WO2011/073122
PCT Pub. Date: Jun. 23, 2011

(65) Prior Publication Data
US 2012/0252077 A1 Oct. 4, 2012

(30) Foreign Application Priority Data
Dec. 14, 2009 (WO) .................. PCT/IB2009/056033

(51) Int. Cl.
C12P 13/12 (2006.01)

(52) U.S. Cl.
CPC .................... *C12P 13/12* (2013.01)

(58) Field of Classification Search
None
See application file for complete search history.

(56) References Cited

U.S. PATENT DOCUMENTS

| 7,238,502 B2 | 7/2007 | Kroeger et al. |
| 2006/0068476 A1 | 3/2006 | Kroger et al. |
| 2006/0068478 A1 | 3/2006 | Schultz et al. |
| 2007/0218524 A1 | 9/2007 | Tomono et al. |

FOREIGN PATENT DOCUMENTS

| DE | 10239073 | 3/2004 |
| DE | 10239308 | 3/2004 |
| JP | 2005-537023 A | 12/2005 |
| JP | 2005-537024 A | 12/2005 |
| WO | 2007/011845 | 1/2007 |
| WO | 2007077041 | 7/2007 |
| WO | 2009-043803 A2 | 4/2009 |
| WO | 2009043372 | 4/2009 |

OTHER PUBLICATIONS

Lerner and Inouye, Nucleic Acids Research, vol. 18, No. 15, p. 4631, 1990.*
International Search Report for PCT/EP2010/069473 Mailed April 21, 2011.
International Search Report for PCT/IB2009/056033 Mailed November 4, 2010.
Saunderson; "Comparative Metabolism of L-Methionine, DL-Methionine and DL-2-Hydroxy 4-Methylthiobutanoic Acid by Broiler Chicks"; British Journal of Nutrition; 1985; vol. 54; p. 621-633.
Sussman et al.; "On a Thermosensitive Repression System in the *Escherichia coli* Lambda Bacteriophage". HEBD, Seances Acad. Sci.; 1962, vol. 254; p. 1517.
Tang et al.; "Microbial Conversion of Glycerol to 1,3-Propanediol by an Engineered Strain of *Escherichia coli*."; Appl Environ Microbiol; Mar. 2009; vol. 75; No. 6; pp. 1628-1634; American Society for Microbiology.
Galkin et al.; "Cleavage of Bacteriophage Gamma CL Repressor Involves the RECA C-Terminal Domain"; J. Mol. Biol.; 2009; vol. 385; pp. 779-787; Elsevier Ltd.
Figge; "Methionine Biosynthesis in *Escherichia coli* and Corynebacterium Glutamicum"; Microbiol Monogr; 2006; vol. 5; pp. 164-185; Springer-Verlag Berlin Heidelberg.
Jechlinger et al. "Altered Temperature Induction Sensitivity of the Lambda PR/CI857 System for Controlled Gene E Expression in *Escherichia coli*" FEMS Microbiology Letters, vol. 173 (1999) 347-352.
Kurnit, David "*Escherichia coli* RECA Deletion Strains That Are Highly Competent for Trnasformation and for In Vivo Phage Packaging", Gene, vol. 82 (1989) 313-315.

* cited by examiner

*Primary Examiner* — Richard Hutson
(74) *Attorney, Agent, or Firm* — Birch, Stewart, Kolasch & Birch, LLP

(57) ABSTRACT

The present invention relates to use of inducible promoters in the production of methionine by fermentation. The present invention concerns a method for the production of methionine, its precursors or derivatives in a fermentative process comprising the following steps:
culturing a modified microorganism in an appropriate culture medium comprising a source of carbon, a source of sulphur and a source of nitrogen, and
recovering methionine and/or its derivatives from the culture medium,
wherein in said modified microorganism, the expression of at least one gene involved in methionine production is under the control, direct or indirect, of a heterologous inducible promoter.
The invention also concerned the modified microorganism used in the method.

9 Claims, No Drawings

USE OF INDUCIBLE PROMOTERS IN THE PRODUCTION OF METHIONINE

CROSS REFERENCE TO RELATED APPLICATIONS

This application is a §371 National Stage Application of PCT/EP2010/069473, filed Dec. 13, 2010, which claims priority to International PCT Application No. PCT/IB2009/056033, filed Dec. 14, 2009.

BACKGROUND OF THE INVENTION

Field of the Invention

The present invention relates to use of inducible promoters in the production of methionine by fermentation.

Background of the Invention

Sulphur-containing compounds such as cysteine, homocysteine, methionine or S-adenosylmethionine are critical to cellular metabolism and are produced industrially to be used as food or feed additives and pharmaceuticals. In particular methionine, an essential amino acid, which cannot be synthesized by animals, plays an important role in many body functions. Aside from its role in protein biosynthesis, methionine is involved in transmethylation and in the bioavailability of selenium and zinc. Methionine is also directly used as a treatment for disorders like allergy and rheumatic fever. Nevertheless most of the methionine that is produced is added to animal feed.

With the decreased use of animal-derived proteins as a result of BSE and chicken flu, the demand for pure methionine has increased. Chemically D,L-methionine is commonly produced from acrolein, methyl mercaptan and hydrogen cyanide. Nevertheless the racemic mixture does not perform as well as pure L-methionine, as for example in chicken feed additives (Saunderson, C. L., (1985) British Journal of Nutrition 54, 621-633). Pure L-methionine can be produced from racemic methionine e.g. through the acylase treatment of N-acetyl-D,L-methionine which increases production costs dramatically. The increasing demand for pure L-methionine coupled to environmental concerns render microbial production of methionine attractive.

Use of inducible promoters in biotechnological processes is in the art of chemical biosynthesis. These promoters usually respond to chemical or physical stimuli exemplified by propionate (WO2007005837), zinc (WO2004020640) and arabinose (WO1998011231) or temperature (Microbial conversion of glycerol to 1,3-propanediol by an engineered strain of *Escherichia coli*. Tang X, Tan Y, Zhu H, Zhao K, Shen W. Appl Environ Microbiol. 2009 March; 75(6):1628-34.) and light, respectively.

Methionine production relies on several precursor providing pathways. Efficient methionine production requires fine tuning of these pathways. For maximum methionine production it can be beneficial to be able to modulate the expression of certain key enzymes during the process. For example (i) the expression of certain enzymes is only required during the production phase and not during the generation of the biomass or vice versa. Other enzymes are only beneficial in stationary phase. Therefore, use of inducible promoters may be of interest in improving the overall yield of producing methionine at an industrial level.

However, due to the complexity of the methionine metabolic pathway and the fine tuning of these pathways for an improved methionine production, use of inducible promoters to control expression of genes involved in methionine production was never considered and reported.

The inventors have found now that inducible promoters may be beneficial when used to regulate gene expression of genes involved in complex metabolic pathways such as methionine biosynthesis.

BRIEF DESCRIPTION OF THE INVENTION

The present invention concerns a method for the production of methionine, its precursors or derivatives in a fermentative process comprising the following steps:
   culturing a modified microorganism in an appropriate culture medium comprising a source of carbon, a source of sulphur and a source of nitrogen, and
   recovering methionine and/or its derivatives from the culture medium,
wherein in said modified microorganism, the expression of at least one gene involved in methionine production is under the control, direct or indirect, of a heterologous inducible promoter.

The invention also concerns the microorganism modified for an improved methionine production in which expression of at least one gene involved in methionine production is under the control, direct or indirect, of a heterologous inducible promoter.

In one particular embodiment, the genes thrA, cysE and metA are under the control, direct or indirect of an heterologous inducible promoter.

DETAILED DESCRIPTION OF THE INVENTION

The present invention is related to a method for the production of methionine, its precursors or derivatives in a fermentative process comprising the following steps:
   culturing a modified microorganism in an appropriate culture medium comprising a source of carbon, a source of sulphur and a source of nitrogen, and
   recovering methionine and/or its derivatives from the culture medium,
wherein in said modified microorganism, the expression of at least one gene involved in methionine production is under the control, direct or indirect, of a heterologous inducible promoter.

According to the invention, the terms 'fermentative process', 'fermentation' or 'culture' are used interchangeably to denote the growth of bacteria on an appropriate growth medium containing a source of carbon, a source of sulphur and a source of nitrogen.

An "appropriate culture medium" is a medium appropriate for the culture and growth of the microorganism. Such media are well known in the art of fermentation of microorganisms, depending upon the microorganism to be cultured.

The term "microorganism" designates a bacterium, yeast or fungus. Preferentially, the microorganism is selected among Enterobacteriaceae, Bacillaceae, Streptomycetaceae and Corynebacteriaceae. More preferentially, the microorganism is a species of *Escherichia, Klebsiella, Pantoea, Salmonella* or *Corynebacterium*. Even more preferentially, the microorganism is either the species *Escherichia coli* or *Corynebacterium glutamicum*.

The term "modified microorganism" is a microorganism modified for an improved methionine production and denotes a microorganism that has been genetically modified with the goal to improve the production yield of methionine. According to the invention, "improved" or "improve" means that the amount of methionine produced by the microorganism, and particularly the methionine yield (ratio of methionine produced per carbon source), is higher in the modified microorganism compared to the corresponding unmodified microorganism. Usual modifications include introducing deletion of genes into microorganisms by transformation and recombination, gene replacements, and introduction of vectors for the expression of heterologous genes.

The modified microorganism used in the method of the invention has both characteristics:
  it is modified for an improved methionine production, and
  expression of at least one gene involved in methionine production is under control, direct or indirect, of an inducible promoter.

The phrase "recovering methionine and/or its derivatives from the culture medium" designates the action of recovering methionine, and possibly S-acyl methionine and N-acyl methionine compounds, such as N-acetyl methionine and N-propionyl methionine, and all other obtained derivatives.

The term "inducible promoter" denotes a promoter whose activity can be increased or decreased upon an external stimulus. Stimuli can be physical or chemical in nature, such as temperature, light, chemicals etc.

Induction of the target gene can be obtained via direct or indirect transmission of the stimulus.

Direct transmission is accomplished when the expression of one target gene is under the control of an inducible promoter.

Indirect transmission can be accomplished by using heterologous RNA-polymerases that are under the control of an inducible promoter and that recognize specific promoters driving the expression of target genes involved in methionine biosynthesis. In this case, the inducible promoter is not directly linked to the promoter of the target gene, but drives the expression of an RNA polymerase transcribing said promoter of the target gene.

These heterologous RNA polymerases can be e.g. T3 RNA polymerase, T7 RNA polymerase or other polymerase known to the expert in the field.

'Indirect transmission' also refers to the 'polar effect' of the inducible expression of one specific gene on the expression of its neighbouring genes. A "polar effect" designates the influence of a genetic modification in a gene on the expression of one or more genes which are downstream said modified gene.

In a specific aspect of the invention, the induction of specific genes involved in methionine production can lead to an induction of genes downstream of said specific genes.

The phrase "under the control of a heterologous inducible promoter" designates the fact that the inducible promoter is not the native promoter of the gene and was introduced in a way to control, at least partially, the level of expression of the gene that is operably linked to it. The activity of an inducible promoter is induced by the presence or absence of biotic or abiotic factors. Expression of genes can be turned on or off, according to the needs of the man skilled in the art. These promoters might be chemically-regulated (in presence of tetracycline, hormones, etc) or physically-regulated, especially by heat or light.

In a specific embodiment of the invention, the expression of at least one gene involved in methionine production is under the direct control of an inducible promoter.

In a first aspect of the invention, the inducible promoter is a physically-inducible promoter, in particular a temperature-inducible promoter or a light-inducible promoter.

The promoter is advantageously a temperature-inducible promoter, preferentially regulated by a modified repressor of phage lambda, the promoter PR or a derivative of PR, the promoter PL or a derivative of PL (A genetic switch. Ptashne M. Blackwell Scientific, Cambridge, Mass. 1986; A genetic switch: Phage lambda revisited. Ptashne M. Cold Spring Harbor Lab Press. Cold Spring Harbor, N.Y. 2004; The bacteriophages, Part II: Life of phages, 8. Gene regulatory circuitry of phage λ. Little J. $2^{nd}$ edition 2004. Richard Calendar. ed. Oxford University Press), and a modified lac promoter regulated by a temperature sensitive Lac repressor.

The repressor represses the expression from the cognate promoter by binding to specific binding sites in the promoter region thereby limiting the access of RNA polymerase to the promoter and reducing initiation or elongation of transcription. Advantageously, said repressor is the lambda repressor allele cI857 (On a thermosensitive repression system in the *Escherichia coli* lambda bacteriophage. Sussman R, Jacob F. C. R. Hebd. Seances Acad. Sci. 1962, 254, p 1517) or another temperature-sensitive allele of the cI lambda repressor.

In a specific aspect of the invention, in the modified microorganism for the production of methionine, the gene encoding recA has been deleted. The protein RecA is known to act as a protease on cI. Therefore the deletion of the gene encoding RecA excludes proteolysis of the lambda repressor cI.

The temperature-inducible promoter might advantageously be chosen between the promoter PR or a derivative, and the promoter PL or a derivative.

In another embodiment, the temperature-inducible promoter is a modified lac promoter regulated by a temperature sensitive Lac repressor.

In a second aspect of the invention, the inducible promoter is chemically-regulated. In particular, the induction of the promoter's activity is linked to changes in the repression of carbon catabolite. Promoters that are activated by carbon catabolite repression are positively regulated via the activator CRP at low concentrations of glucose or in the absence of glucose.

Advantageously, the inducible promoter is induced by the presence of carbon sources or of sugar alcohols. Examples of promoters that are induced by carbon sources or sugar alcohols include the arabinose or raffinose promoter and the mannitol promoter or glucitol promoters, respectively.

According to a specific aspect of the invention, the expression of genes of interest is regulated via "indirect transmission", i.e at least one gene involved in methionine production is transcribed by a heterologous RNA polymerase whose expression is under the control of an inducible promoter.

In a specific embodiment of the invention, the heterologous RNA polymerase is chosen from T7, T3 polymerase.

According to the invention, at least one gene involved in methionine production or the production of its precursors is under the control, direct or indirect, of a heterologous inducible promoter; as previously explained, either the gene is under the direct control of an inducible promoter, or the gene is transcribed by an inducible RNA polymerase or both combinations.

Genes involved in methionine production in a microorganism are known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor-providing pathways. Methionine producing strains have been described in patent applications WO 2005/111202, WO 2007/077041, WO 2009/043803 and WO 2009/043372 and are incorporated as reference into this application.

A methionine producing strain that overexpresses homoserine succinyltransferase alleles with reduced feed-back sensitivity to its inhibitors SAM and methionine is described in patent application WO 2005/111202. This application describes also the combination of these alleles with a deletion of the methionine repressor MetJ (GenBank 1790373), responsible for the down-regulation of the methionine regulon as was suggested in patent application JP 2000/157267. In addition, combinations of the two modifications with the overexpression of aspartokinase/homoserine dehydrogenase are described in patent application WO 2005/111202.

The overexpression of the genes cysE, metH and metF has been suggested in WO 2007/077041.

To increase methionine production, at least one of the following genes involved in methionine production may be under the control of an inducible promoter.

a) The expression of genes involved in sulphur assimilation may advantageously be under the control of an inducible promoter or of a RNA polymerase:

| gene | accession number | function |
| --- | --- | --- |
| cysK | 1788754 | cysteine synthase |
| cysZ | g1788753 | ORF upstream of cysK |
| cysN | g1789108 | ATP sulfurylase |
| cysD | g1789109 | sulfate adenylyltransferase |
| cysC | g1789107 | adenylylsulfate kinase |
| cysZ | 1788753 | sulfate transport |
| sbp | 1790351 | Periplasmic sulfate-binding protein | b) Anaplerotic reactions may be boosted by expressing the following genes:

| ppc | 1790393 | phosphoenolpyruvate carboxylase |
| --- | --- | --- |
| pps | 1787994 | phosphoenolpyruvate synthase |
| pyc | CAB13359 | pyruvate carboxylase (e.g from *B. subtilis*) | c) Acetate consuming reactions may be boosted by over expressing the gene:

| acs | 1790505 | acetyl-CoA synthetase |
| --- | --- | --- | d) Enzymes directly involved in methionine biosynthesis:

| metA | 1790443 | homoserine O-transsuccinylase |
| --- | --- | --- |
| metB | 1790375 | cystathionine gamma-synthase |
| metC | 1789383 | cystathionine beta-lyase |
| metE | 2367304 | 5-methyltetrahydropteroyltriglutamate-homocysteine S-methyltransferase |
| metF | 1790377 | 5,10-methylenetetrahydrofolate reductase |
| metH | 1790450 | B12-dependent homocysteine-N5-methyltetrahydrofolate transmethylase, |
| metK | 1789311 | methionine adenosyltransferase |
| metL | 1790376 | aspartokinase II/homoserine dehydrogenase II | e) Enzymes involved in aspartate metabolism:

| asd | 1789841 | aspartate-semialdehyde dehydrogenase |
| --- | --- | --- |
| aspC | 1787159 | aspartate aminotransferase |
| lysC | 1790455 | aspartokinase III |

In a preferred embodiment of the invention, the expression of at least one of the genes thrA and/or cysE is under the control of an inducible promoter, directly or indirectly.

The enzyme ThrA or any of its homologues (MetL, LysC) catalyze reactions in the transformation of aspartate to homoserine, a precursor of methionine. The enzyme CysE catalyzes the O-acetylation of serine to form O-acetyl-serine that is the direct precursor of cysteine that in turn serves as sulphur donor for methionine biosynthesis.

Production of methionine may be further increased by using an altered metB allele that uses preferentially or exclusively $H_2S$ and thus produces homocysteine from O-succinyl-homoserine as described in the patent application WO 2004/076659 that is incorporated herein by reference.

Further increase in methionine production may be obtained by attenuating the expression of the genes pykA, pykF and/or purU as described in patent application WO2009043803. This can also be accomplished by using an inducible promoter, directly or indirectly.

This application also describes methionine-producing strains in which the operons cysPUWAM, cysJIH and gcvTHP and the genes serA, serB, serC, lpd and glyA are overexpressed. Similarly this can be accomplished by using an inducible promoter, directly or indirectly.

Furthermore expression of genes in pathways degrading methionine (see list below) or deviating from the methionine production pathway may be attenuated using an inducible promoter, directly or indirectly. Attenuation in this context describes the reduction of the intracellular activity of an enzyme by measures such as reducing its expression, reducing the stability of the enzyme, increasing its degradation and/or other solutions known to the expert in the field. This can be accomplished by reducing the expression of the inducible promoter, i.e. eliminating the stimulus that induces the inducible promoter or reducing the expression of the inducible RNA polymerase.

| Gene | Genbank entry | activity |
| --- | --- | --- |
| ackA | 1788633 | acetate kinase |
| pta | 1788635 | phosphotransacetylase |
| aceE | 1786304 | pyruvate deydrogenase E1 |
| aceF | 1786305 | pyruvate deydrogenase E2 |
| lpd | 1786307 | pyruvate deydrogenase E3 |
| sucC | 1786948 | succinyl-CoA synthetase, beta subunit |
| sucD | 1786949 | succinyl-CoA synthetase, alpha subunit |
| pck | 1789807 | phosphoenolpyruvate carboxykinase |
| maeB | | |
| poxB | 1787096 | pyruvate oxidase |
| ilvB | 1790104 | acetohydroxy acid synthase I, large subunit |
| ilvN | 1790103 | acetohydroxy acid synthase I, small subunit |
| ilvG | 1790202 1790203 | acetohydroxy acid synthase II, large subunit |
| ilvM | 1790204 | acetohydroxy acid synthase II, small subunit |
| ilvI | 1786265 | acetohydroxy acid synthase III, large subunit |
| ilvH | 1786266 | acetohydroxy acid synthase III, small subunit |
| aroF | 1788953 | DAHP synthetase |
| aroG | 1786969 | DAHP synthetase |
| aroH | 1787996 | DAHP synthetase |
| thrB | 1786184 | homoserine kinase |
| thrC | 1786185 | threonine synthase |
| sdaA | 1788116 | serine deaminase |
| sdaB | 1789161 | serine deaminase |
| speD | 1786311 | S-Adenosylmethionine decarboxylase |
| speC | 1789337 | ornithine decarboxylase |
| astA | 1788043 | arginine succinyltransferase |
| dapA | 1788823 | dihydrodipicolinate synthase |
| mdh | 1789632 | malate dehydrogenase |
| mqo | 1788539 | malate dehydrogenase, FAD/NAD(P)-binding domain |

-continued

| Gene | Genbank entry | activity |
|---|---|---|
| gltA | 1786939 | citrate synthase |
| aceE | 1786304 | pyruvate dehydrogenase, E1 |
| aceF | 1786305 | pyruvate dehydrogenase, E2 |

In a preferred embodiment of the invention, the expression of at least one of the genes: thrA, cysE, metA, is under the control of an inducible promoter, directly or indirectly. In another specific embodiment, the genes thrA, cysE and metA are under control of an inducible promoter, directly or indirectly. In a preferred embodiment of the invention, the expression of thrA gene is under direct control of an inducible promoter, and the expression of cysE gene is under a 'polar effect' of inducible expression of the thrA gene. In another preferred embodiment of the invention, the expression of thrA gene is under direct control of an inducible promoter, and the expressions of cysE and metA genes are under 'polar effect' of inducible expression of thrA gene.

In a specific embodiment, the three genes thrA, cysE and metA are under control of the same inducible promoter, such as the temperature inducible promoters disclosed above and in the examples.

In the invention, "thrA gene" means native thrA gene or thrA alleles with reduced feed-back sensitivity to threonine, such as described in WO2005/108561. According to the invention, "metA gene" means native metA genes or metA mutant alleles encoding enzyme with reduced feed-back sensitivity to methionine and S-adenosylmethionine, such as described in WO2005/108561.

Genes controlled by the inducible promoter may either be at its native position on the chromosome or integrated at a non-native position. One or several integrations of the gene controlled by the inducible promoter may be required for optimal methionine production. Similarly, one or several copies of the regulator gene may be required for optimal expression. Different ratios of repressor gene copies and promoters may be used to fine-tune expression.

The gene under the control of the inducible promoter is preferentially integrated into loci, whose modification does not have a negative impact on methionine production. Examples for loci into which the gene may be integrated are:

| Locus | Accession Number | Function |
|---|---|---|
| aaaD | 87081759 | Pseudogene, phage terminase protein A homolog, N-terminal fragment |
| aaaE | 1787395 | Pseudogene, phage terminase protein A homolog, C-terminal fragment |
| afuB | 1786458 | Pseudogene, ferric ABC family transporter permease; C-terminal fragment |
| afuC | 87081709 | predicted ferric ABC transporter subunit (ATP-binding component) |
| agaA | 48994927 | Pseudogene, C-terminal fragment, GalNAc-6-P deacetylase |
| agaW | 1789522 | Pseudogene, N-terminal fragment, PTS system EIICGalNAc |
| alpA | 1788977 | protease |
| appY | 1786776 | DNA-binding transcriptional activator |
| argF | 1786469 | ornithine carbamoyltransferase |
| argU | none | arginine tRNA |
| argW | none | Arginine tRNA(CCU) 5 |
| arpB | 87081959 | Pseudogene reconstruction, ankyrin repeats |
| arrD | 1786768 | lysozyme |
| arrQ | 1787836 | Phage lambda lysozyme R protein homolog |
| arsB | 87082277 | arsenite transporter |
| arsC | 1789918 | arsenate reductase |
| arsR | 1789916 | DNA-binding transcriptional repressor |
| beeE | 1787397 | Pseudogene, N-terminal fragment, portal protein |
| borD | 1786770 | bacteriophage lambda Bor protein homolog |
| cohE | 1787391 | CI-like repressor |
| croE | 87081841 | Cro-like repressor |
| cspB | 1787839 | Cold shock protein |
| cspF | 1787840 | Cold shock protein homolog |
| cspI | 1787834 | Cold shock protein |
| cybC | 1790684 | Pseudogene, N-terminal fragment, cytochrome b562 |
| dicA | 1787853 | Regulatory for dicB |
| dicB | 1787857 | Control of cell division |
| dicC | 1787852 | Regulatory for dicB |
| dicF | none | DicF antisense sRNA |
| eaeH | 1786488 | Pseudogene, intimin homolog |
| efeU | 87081821 | Pseudogene reconstruction, ferrous iron permease |
| emrE | 1786755 | multidrug resistance pump |
| essD | 1786767 | predicted phage lysis protein |
| essQ | 87081934 | Phage lambda S lysis protein homolog |
| exoD | 1786750 | Pseudogene, C-terminal exonuclease fragment |
| eyeA | none | novel sRNA, unknown function |
| flu | 48994897 | Antigen 43 |
| flxA | 1787849 | unknown |
| gapC | 87081902 | Pseudogene reconstruction, GAP dehydrogenase |
| gatR | 87082039 | Pseudogene reconstruction, repressor for gat operon |
| glvC | 1790116 | Pseudogene reconstruction |
| glvG | 1790115 | Pseudogene reconstruction, 6-phospho-beta-glucosidase |
| gnsB | 87081932 | Multicopy suppressor of secG(Cs) and fabA6(Ts) |
| gtrA | 1788691 | Bactoprenol-linked glucose translocase |
| gtrB | 1788692 | Bactoprenol glucosyl transferase |
| gtrS | 1788693 | glucosyl transferase |
| hokD | 1787845 | Small toxic membrane polypeptide |
| icd | 1787381 | Isocitrate dehydrogenase |
| icdC | 87081844 | pseudogene |
| ilvG | 87082328 | Pseudogene reconstruction, acetohydroxy acid synthase II |

-continued

| Locus | Accession Number | Function |
|---|---|---|
| insA | 1786204 | IS1 gene, transposition function |
| insA | 1786204 | IS1 gene, transposition function |
| insB | 1786203 | IS1 insertion sequence transposase |
| insB | 1786203 | IS1 insertion sequence transposase |
| insC | 1786557 | IS2 gene, transposition function |
| insD | 1786558 | IS2 gene, transposition function |
| insD | 1786558 | IS2 gene, transposition function |
| insE | 1786489 | IS3 gene, transposition function |
| insF | 1786490 | IS3 gene, transposition function |
| insH | 1786453 | IS5 gene, transposition function |
| insH | 1786453 | IS5 gene, transposition function |
| insH | 1786453 | IS5 gene, transposition function |
| insI | 1786450 | IS30 gene, transposition function |
| insI(−1) | 1786450 | IS30 gene, transposition function |
| insM | 87082409 | Pseudogene, truncated IS600 transposase |
| insN | 1786449 | Pseudogene reconstruction, IS911 transposase ORFAB |
| insO | none | Pseudogene reconstruction, IS911 transposase ORFAB |
| insX | 87081710 | Pseudogene, IS3 family transposase, N-terminal fragment |
| insZ | 1787491 | Pseudogene reconstruction, IS4 transposase family, in ISZ' |
| intA | 1788974 | Integrase gene |
| intB | 1790722 | Pseudogene reconstruction, P4-like integrase |
| intD | 1786748 | predicted integrase |
| intE | 1787386 | e14 integrase |
| intF | 2367104 | predicted phage integrase |
| intG | 1788246 | Pseudogene, integrase homolog |
| intK | 1787850 | Pseudogene, integrase fragment |
| intQ | 1787861 | Pseudogene, integrase fragment |
| intR | 1787607 | Integrase gene |
| intS | 1788690 | Integrase |
| intZ | 1788783 | Putative integrase gene |
| isrC | none | Novel sRNA, function unknown |
| jayE | 87081842 | Pseudogene, C-terminal fragment, baseplate |
| kilR | 87081884 | Killing function of the Rac prophage |
| lafU | none | Pseudogene, lateral flagellar motor protein fragment |
| lfhA | 87081703 | Pseudogene, lateral flagellar assembly protein fragment |
| lit | 1787385 | Cell death peptidase |
| lomR | 1787632 | Pseudogene reconstruction, lom homolog; outer membrane protein interrupted by IS5Y, missing N-terminus |
| malS | 1789995 | α-amylase |
| mcrA | 1787406 | 5-methylcytosine-specific DNA binding protein |
| mdtQ | 87082057 | Pseudogene reconstruction, lipoprotein drug pump OMF family |
| melB | 1790561 | melibiose permease |
| mmuM | 1786456 | homocysteine methyltransferase |
| mmuP | 870811708 | S-methylmethionine permease |
| mokA | none | Pseudogene, overlapping regulatory peptide, enables hokB |
| ninE | 1786760 | unknown |
| nmpC | 1786765 | Pseudogene reconstruction, OM porin, interrupted by IS5B |
| nohD | 1786773 | DNA packaging protein |
| nohQ | 1787830 | Pseudogene, phage lambda Nu1 homolog, terminase small subunit family, putative DNA packaging protein |
| ogrK | 1788398 | Positive regulator of P2 growth |
| ompT | 1786777 | outer membrane protease VII |
| oweE | none | Pseudogene, lambda replication protein O homolog |
| oweS | 1788700 | Pseudogene, lambda replication protein O homolog |
| pauD | none | argU pseudogene, DLP12 prophage attachment site |
| pawZ | none | CPS-53 prophage attachment site attR, argW pseudogene |
| pbl | 87082169 | Pseudogene reconstruction, pilT homolog |
| peaD | 87081754 | Pseudogene, phage lambda replication protein P family; C-terminal fragment |
| perR | 1786448 | predicted DNA-binding transcriptional regulator |
| pgaA | 1787261 | outer membrane porin of poly-β-1,6-N-acetyl-D-glucosamine (PGA) biosynthesis pathway |
| pgaB | 1787260 | PGA N-deacetylase |
| pgaC | 1787259 | UDP-N-acetyl-D-glucosamine β-1,6-N-acetyl-D-glucosaminyl transferase |
| pgaD | 1787258 | predicted inner membrane protein |
| phnE | 87082370 | Pseudogene reconstruction, phosphonate permease |
| pinE | 1787404 | DNA invertase |
| pinH | 1789002 | Pseudogene, DNA invertase, site-specific recombination |
| pinQ | 1787827 | DNA invertase |
| pinR | 1787638 | DNA invertase |
| prfH | 1786431 | Pseudogene, protein release factor homolog |
| psaA | none | ssrA pseudogene, CP4-57 attachment site duplication |
| ptwF | none | thrW pseudogene, CP4-6 prophage attachment site |
| quuD | 1786763 | predicted antitermination protein |
| quuQ | 87081935 | Lambda Q antitermination protein homolog |
| racC | 1787614 | unknown |
| racR | 1787619 | Rac prophage repressor, cI-like |

-continued

| Locus | Accession Number | Function |
|---|---|---|
| ralR | 1787610 | Restriction alleviation gene |
| rbsA | 1790190 | D-ribose ABC transporter subunit (ATP-binding component) |
| rbsD | 87082327 | D-ribose pyranase |
| recE | 1787612 | RecET recombinase |
| recT | 1787611 | RecET recombinase |
| relB | 1787847 | Antitoxin for RelE |
| relE | 1787846 | Sequence-specific mRNA endoribonuclease |
| rem | 1787844 | unknown |
| renD | 87081755 | Pseudogene reconstruction, lambda ren homolog, interrupted by IS3C; putative activator of lit transcription |
| rhsE | 1787728 | Pseudogene, rhs family, encoded within RhsE repeat |
| rnlA | 1788983 | RNase LS, endoribonuclease |
| rph | 1790074 | Pseudogene reconstruction, RNase PH |
| rusA | 1786762 | Endonuclease |
| rzoD | 87081757 | Probable Rzl-like lipoprotein |
| rzoQ | none | Probable Rzl-like lipoprotein |
| rzoR | 87081890 | Probable Rzl-like lipoprotein |
| rzpD | 1786769 | predicted murein endopeptidase |
| rzpQ | 1787835 | Rz-like equivalent |
| rzpR | 87081889 | Pseudogene, Rz homolog |
| sieB | 87081885 | Superinfection exclusion protein |
| sokA | none | Pseudogene, antisense sRNA blocking mokA/hokA translation |
| stfE | 87081843 | C-terminal Stf variable cassette, alternate virion-host specificity protein; Tail Collar domain, pseudogene |
| stfP | 1787400 | Predicted tail fiber protein |
| stfR | 87081892 | Side-tail fiber protein |
| tfaD | 87081759 | Pseudogene, tail fiber assembly gene, C-terminal fragment |
| tfaE | 1787402 | Predicted tail fiber assembly gene |
| tfaP | 1787401 | Predicted tail fiber assembly gene |
| tfaQ | 2367120 | Phage lambda tail fiber assembly gene homolog |
| tfaR | 1787637 | Phage lambda tail fiber assembly gene homolog |
| tfaS | 87082088 | Pseudogene, tail fiber assembly gene, C-terminal fragment |
| tfaX | 2367110 | Pseudogene reconstruction, tail fiber assembly gene, C-terminal fragment |
| thrW | none | threonine tRNA (attachment site of the CP4-6 prophage) |
| torI | 87082092 | CPS-53/KpLE1 exisionase |
| treB | 2367362 | subunit of trehalose PTS permease (IIB/IIC domains) |
| treC | 1790687 | trehalose-6-phosphate hydrolase |
| trkG | 1787626 | Major constitutive K+ uptake permease |
| ttcA | 1787607 | Integrase gene |
| ttcC | none | Pseudogene, prophage Rac integration site ttcA duplication |
| uidB | 1787902 | Glucuronide permease, inactive point mutant |
| uxaA | 1789475 | altronate hydrolase |
| uxaC | 2367192 | uronate isomerase |
| wbbL | 1788343 | Pseudogene reconstruction, rhamnosyl transferase |
| wcaM | 1788356 | predicted colanic acid biosynthesis protein |
| xisD | none | Pseudogene, exisionase fragment in defective prophage DLP12 |
| xisE | 1787387 | e14 excisionase |
| yabP | 1786242 | Pseudogene reconstruction |
| yafF | 87081701 | Pseudogene, C-terminal fragment, H repeat-associated protein |
| yafU | 1786411 | Pseudogene, C-terminal fragment |
| yafW | 1786440 | antitoxin of the YkfI-YafW toxin-antitoxin system |
| yafX | 1786442 | unknown |
| yafY | 1786445 | predicted DNA-binding transcriptional regulator; inner membrane lipoprotein |
| yafZ | 87081705 | unknown |
| yagA | 1786462 | predicted DNA-binding transcriptional regulator |
| yagB | 87081711 | Pseudogene, antitoxin-related, N-terminal fragment |
| yagE | 1786463 | predicted lyase/synthase |
| yagF | 1786464 | predicted dehydratase |
| yagG | 1786466 | putative sugar symporter |
| yagH | 1786467 | putative β-xylosidase |
| yagI | 1786468 | predicted DNA-binding transcriptional regulator |
| yagJ | 1786472 | unknown |
| yagK | 1786473 | unknown |
| yagL | 1786474 | DNA-binding protein |
| yagM | 2367101 | unknown |
| yagN | 2367102 | unknown |
| yagP | 1786476 | Pseudogene, LysR family, fragment |
| yaiT | 1786569 | Pseudogene reconstruction, autotransporter family |
| yaiX | 87082443 | Pseudogene reconstruction, interrupted by IS2A |
| ybbD | 1786709 | Pseudogene reconstruction, novel conserved family |
| ybcK | 1786756 | predicted recombinase |
| ybcL | 1786757 | predicted kinase inhibitor |
| ybcM | 1786758 | predicted DNA-binding transcriptional regulator |
| ybcN | 1786759 | DNA base-flipping protein |
| ybcO | 1786761 | unknown |
| ybcV | 87081758 | unknown |

-continued

| Locus | Accession Number | Function |
|---|---|---|
| ybcW | 1786772 | unknown |
| ybcY | 48994878 | Pseudogene reconstruction, methyltransferase family |
| ybeM | 1786843 | Pseudogene reconstruction, putative CN hydrolase |
| ybfG | 87081771 | Pseudogene reconstruction, novel conserved family |
| ybfI | none | Pseudogene reconstruction, KdpE homolog |
| ybfL | 87081775 | Pseudogene reconstruction, H repeat-associated protein |
| ybfO | 1786921 | Pseudogene, copy of Rhs core with unique extension |
| ycgH | 87081847 | Pseudogene reconstruction |
| ycgI | 1787421 | Pseudogene reconstruction, autotransporter homolog |
| ycjV | 1787577 | Pseudogene reconstruction, malK paralog |
| ydaC | 1787609 | unknown |
| ydaE | 87081883 | Metallothionein |
| ydaF | 87081886 | unknown |
| ydaG | 87081887 | unknown |
| ydaQ | 87081882 | Putative exisionase |
| ydaS | 1787620 | unknown |
| ydaT | 1787621 | unknown |
| ydaU | 1787622 | unknown |
| ydaV | 1787623 | unknown |
| ydaW | 87081888 | Pseudogene, N-terminal fragment |
| ydaY | 1787629 | pseudogene |
| ydbA | 87081898 | Pseudogene reconstruction, autotransporter homolog |
| yddK | 1787745 | Pseudogene, C-terminal fragment, leucine-rich |
| yddL | 1787746 | Pseudogene, OmpCFN porin family, N-terminal fragment |
| ydeT | 1787782 | Pseudogene, FimD family, C-terminal fragment |
| ydfA | 1787854 | unknown |
| ydfB | 87081937 | unknown |
| ydfC | 1787856 | unknown |
| ydfD | 1787858 | unknown |
| ydfE | 1787859 | Pseudogene, N-terminal fragment |
| ydfJ | 1787824 | Pseudogene reconstruction, MFS family |
| ydfK | 1787826 | Cold shock gene |
| ydfO | 87081931 | unknown |
| ydfR | 1787837 | unknown |
| ydfU | 87081936 | unknown |
| ydfV | 1787848 | unknown |
| ydfX | 1787851 | pseudogene |
| yedN | 87082002 | Pseudogene reconstruction, IpaH/YopM family |
| yedS | 87082009 | Pseudogene reconstruction, outer membrane protein homolog |
| yeeH | none | Pseudogene, internal fragment |
| yeeL | 87082016 | Pseudogene reconstruction, glycosyltransferase family |
| yeeP | 87082019 | Pseudogene, putative GTP-binding protein |
| yeeR | 87082020 | unknown |
| yeeS | 1788312 | unknown |
| yeeT | 1788313 | unknown |
| yeeU | 1788314 | Antitoxin component of toxin-antitoxin protein pair YeeV-YeeU |
| yeeV | 1788315 | Toxin component of toxin-antitoxin protein pair YeeV-YeeU |
| yeeW | 1788316 | pseudogene |
| yegZ | none | Pseudogene, gpD phage P2-like protein D; C-terminal fragment |
| yehH | 87082046 | Pseudogene reconstruction |
| yehQ | 87082050 | Pseudogene reconstruction |
| yejO | 1788516 | Pseudogene reconstruction, autotransporter homolog |
| yfaH | 1788571 | Pseudogene reconstruction, C-terminal fragment, LysR homolog |
| yfaS | 87082066 | Pseudogene reconstruction |
| yfcU | 1788678 | Pseudogene reconstruction, FimD family |
| yfdK | 1788696 | unknown |
| yfdL | 1788697 | Pseudogene, tail fiber protein |
| yfdM | 87082089 | Pseudogene, intact gene encodes a predicted DNA adenine methyltransferase |
| yfdN | 1788699 | unknown |
| yfdP | 1788701 | unknown |
| yfdQ | 1788702 | unknown |
| yfdR | 87082090 | unknown |
| yfdS | 1788704 | unknown |
| yfdT | 1788705 | unknown |
| yffL | 1788784 | unknown |
| yffM | 1788785 | unknown |
| yffN | 1788786 | unknown |
| yffO | 1788787 | unknown |
| yffP | 1788788 | unknown |
| yffQ | 1788790 | unknown |
| yffR | 1788791 | unknown |
| yffS | 1788792 | unknown |
| yfjH | 1788976 | unknown |
| yfjI | 1788978 | unknown |
| yfjJ | 1788979 | unknown |
| yfjK | 1788980 | unknown |

-continued

| Locus | Accession Number | Function |
|---|---|---|
| yfjL | 1788981 | unknown |
| yfjM | 1788982 | unknown |
| yfjO | 87082140 | unknown |
| yfjP | 48994902 | unknown |
| yfjQ | 1788987 | unknown |
| yfjR | 1788988 | unknown |
| yfjS | 87082142 | unknown |
| yfjT | 1788990 | unknown |
| yfjU | 1788991 | pseudogene |
| yfjV | 1788992 | Pseudogene reconstruction, arsB-like C-terminal fragment |
| yfjW | 2367146 | unknown |
| yfjX | 1788996 | unknown |
| yfjY | 1788997 | unknown |
| yfjZ | 1788998 | Antitoxin component of putative toxin-antitoxin YpjF-YfjZ |
| ygaQ | 1789007 | Pseudogene reconstruction, has alpha-amylase-related domain |
| ygaY | 1789035 | Pseudogene reconstruction, MFS family |
| ygeF | 2367169 | Pseudogene reconstruction, part of T3SS PAI ETT2 remnant |
| ygeK | 87082170 | Pseudogene reconstruction, part of T3SS PAI ETT2 remnant |
| ygeN | 1789221 | Pseudogene reconstruction, orgB homolog |
| ygeO | 1789223 | Pseudogene, orgA homolog, part of T3SS PAI ETT2 remnant |
| ygeQ | 1789226 | Pseudogene reconstruction, part of T3SS PAI ETT2 remnant |
| yghE | 1789340 | Pseudogene reconstruction, general secretion protein family |
| yghF | 1789341 | Pseudogene, general secretion protein |
| yghO | 1789354 | Pseudogene, C-terminal fragment |
| yghX | 1789373 | Pseudogene reconstruction, S9 peptidase family |
| yhcE | 1789611 | Pseudogene reconstruction, interrupted by IS5R |
| yhdW | 1789668 | Pseudogene reconstruction |
| yhiL | 87082275 | Pseudogene reconstruction, FliA regulated |
| yhiS | 1789920 | Pseudogene reconstruction, interrupted by IS5T |
| yhjQ | 1789955 | Pseudogene reconstruction |
| yibJ | 48994952 | Pseudogene reconstruction, Rhs family |
| yibS | none | Pseudogene reconstruction, Rhs family, C-terminal fragment |
| yibU | none | Pseudogene reconstruction, H repeat-associated protein |
| yibW | none | Pseudogene reconstruction, rhsA-linked |
| yicT | none | Pseudogene, N-terminal fragment |
| yifN | 2367279 | Pseudogene reconstruction |
| yjbI | 1790471 | Pseudogene reconstruction |
| yjdQ | none | Pseudogene reconstruction, P4-like integrase remnant |
| yjgX | 1790726 | Pseudogene reconstruction, EptAB family |
| yjhD | 87082406 | Pseudogene, C-terminal fragment |
| yjhE | 87082407 | Pseudogene, putative transporter remnant |
| yjhR | 1790762 | Pseudogene reconstruction, helicase family, C-terminal fragment |
| yjhV | 1790738 | Pseudogene, C-terminal fragment |
| yjhY | none | Pseudogene reconstruction, novel zinc finger family |
| yjhZ | none | Pseudogene reconstruction, rimK paralog, C-terminal fragment |
| yjiP | 1790795 | Pseudogene reconstruction, transposase family |
| yjiT | 87082428 | Pseudogene, N-terminal fragment |
| yjiV | none | Pseudogene reconstruction, helicase-like, C-terminal fragment |
| yjjN | 87082432 | predicted oxidoreductase |
| ykfA | 87081706 | putative GTP-binding protein |
| ykfB | 1786444 | unknown |
| ykfC | 87081707 | Pseudogene, retron-type reverse transcriptase family, N-terminal fragment |
| ykfF | 1786443 | unknown |
| ykfG | 2367100 | unknown |
| ykfH | 87081704 | unknown |
| ykfI | 1786439 | toxin of the YkfI-YafW toxin-antitoxin system |
| ykfJ | 1786430 | Pseudogene, N-terminal fragment |
| ykfK | 1786445 | Pseudogene, N-terminal fragment |
| ykfL | none | Pseudogene, C-terminal fragment |
| ykfN | none | Pseudogene, N-terminal remnant, YdiA family |
| ykgA | 87081714 | Pseudogene, N-terminal fragment, AraC family |
| ykgP | none | Pseudogene, oxidoreductase fragment |
| ykgQ | none | Pseudogene, C-terminal fragment of a putative dehydrogenase |
| ykgS | none | Pseudogene internal fragment |
| ykiA | 1786591 | Pseudogene, C-terminal fragment |
| ylbE | 1786730 | Pseudogene reconstruction, yahG paralog |
| ylbG | 87081748 | Pseudogene reconstruction, discontinuous N-terminal fragment |
| ylbH | 1786708 | Pseudogene, copy of Rhs core with unique extension |
| ylbI | none | Pseudogene, internal fragment, Rhs family |
| ylcG | 87081756 | unknown |
| ylcH | none | unknown |
| ylcI | none | unknown |
| ymdE | 87081823 | Pseudogene, C-terminal fragment |
| ymfD | 1787383 | Putative SAM-dependent methyltransferase |
| ymfE | 1787384 | unknown |
| ymfI | 87081839 | unknown |

-continued

| Locus | Accession Number | Function |
|---|---|---|
| ymfJ | 87081840 | unknown |
| ymfL | 1787393 | unknown |
| ymfM | 1787394 | unknown |
| ymfQ | 1787399 | Putative baseplate or tail fiber proteintt |
| ymfR | 1787396 | unknown |
| ymjC | none | Pseudogene, N-terminal fragment |
| ymjD | none | Expressed deletion pseudogene fusion remnant protein |
| ynaA | 1787631 | Pseudogene, N-terminal fragment |
| ynaE | 1787639 | Cold shock gene |
| ynaK | 1787628 | unknown |
| yncI | 1787731 | Pseudogene reconstruction, H repeat-associated, RhsE-linked |
| yncK | none | Pseudogene reconstruction, transposase homolog |
| yneL | 1787784 | Pseudogene reconstruction, C-terminal fragment, AraC family |
| yneO | 1787788 | Pseudogene reconstruction, putative OM autotransporter adhesi |
| ynfN | 87081933 | Cold shock gene |
| ynfO | none | unknown |
| yoeA | 87082018 | Pseudogene reconstruction, interrupted by IS2F |
| yoeD | none | Pseudogene, C-terminal fragment of a putative transposase |
| yoeF | 87082021 | Pseudogene, C-terminal fragment |
| yoeG | none | pseudogene, N-terminal fragment |
| yoeH | none | pseudogene, C-terminal fragment |
| ypdJ | 87082091 | Pseudogene, exisonase fragment |
| ypjC | 1789003 | Pseudogene reconstruction |
| ypjF | 1788999 | Toxin component of putative toxin-antitoxin pair YpjF-YfjZ |
| ypjI | none | Pseudogene reconstruction |
| ypjJ | 87082144 | unknown |
| ypjK | 87082141 | unknown |
| yqfE | 1789281 | Pseudogene reconstruction, C-terminal fragment, LysR family |
| yqiG | 48994919 | Pseudogene reconstruction, FimD family, interrupted by IS2I |
| yrdE | none | Pseudogene reconstruction, C-terminal fragment, yedZ paralog |
| yrdF | none | Pseudogene, N-terminal fragment |
| yrhA | 87082266 | Pseudogene reconstruction, interrupted by IS1E |
| yrhC | 87082273 | Pseudogene reconstruction, N-terminal fragment |
| ysaC | none | Pseudogene, C-terminal remnant |
| ysaD | none | Pseudogene, internal sequence remnant |
| ytfA | 1790650 | Pseudogene, C-terminal fragment |
| yzgL | 87082264 | Pseudogene, putative periplasmic solute binding protein |

In the description of the present invention, genes and proteins are identified using the denominations of the corresponding genes in E. coli. However, and unless specified otherwise, use of these denominations has a more general meaning according to the invention and covers all the corresponding genes and proteins in other organisms, more particularly microorganisms.

Using the references given in GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. $2^{nd}$ ed. Cold Spring Harbor Lab., Cold Spring Harbor, N.Y.)

PFAM (protein families database of alignments and hidden Markov models available on the SANGER website represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; available on the National Center for Biotechnology Information (NCBI) website are obtained by comparing protein sequences from fully sequenced genomes representing major phylogenic lines. Each COG is defined from at least three lines, which permits the identification of former conserved domains.

The means of identifying homologous sequences and their percentage homologies are well known to those skilled in the art, and include in particular the BLAST programs, which are available on the National Center for Biotechnology Information (NCBI) website with the default parameters indicated on that website. The sequences obtained can then be exploited (e.g., aligned) using, for example, the programs CLUSTALW available on the European Bioinformatics Institute (EBI) website or MULTALIN bioinfo.genotoul.fr/multalin/multalin.html), with the default parameters indicated on those websites.

The method for the production of methionine, its precursors or derivatives in a fermentative process, is well known by the man skilled in the art. Different factors of the fermentative process can be modulated for the optimization of the process, such as the choice of the sulfur source, of the carbon source, and of the nitrogen source.

In a preferred aspect of the invention, the sulphur source used for the fermentative production of L-methionine, added in the culture medium, is sulfate, thiosulfate, hydrogen sulfide, dithionate, dithionite, sulfite, methylmercaptan, dimethyldisulfide and other methyl capped sulfides or a combination of the different sources.

More preferentially, the sulphur source in the culture medium is sulfate or thiosulfate, or a mixture thereof.

The term 'carbon source' according to the present invention denotes any source of carbon that can be used by those skilled in the art to support the normal growth of a microorganism, which can be hexoses (such as glucose, galactose or lactose), pentoses, monosaccharides, disaccharides (such as sucrose, cellobiose or maltose), oligosaccharides, molasses, starch or its derivatives, hemicelluloses, glycerol and combinations thereof. An especially preferred carbon source is glucose. Another preferred carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product.

The term nitrogen source corresponds to either an ammonium salt or ammoniac gas.

The nitrogen source is supplied in the form of ammonium or ammoniac.

The fermentation is generally conducted in fermenters with an appropriate culture medium adapted to the microorganism being used, containing at least one simple carbon source, and if necessary co-substrates for the production of metabolites.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

As an example of known culture medium for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As an example of known culture medium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

The present invention is also related to a method for the production of methionine, comprising the step of isolation of methionine, its precursors or derivatives, of the fermentation broth and/or the biomass, optionally remaining in portions or in the total amount (0-100%) in the end product.

In a specific aspect of the invention, the culture is performed in such conditions that the microorganism is limited or starved for an inorganic substrate, in particular phosphate and/or potassium.

Subjecting an organism to a limitation of an inorganic substrate defines a condition under which growth of the microorganisms is governed by the quantity of an inorganic chemical supplied that still permits weak growth.

Starving a microorganism for an inorganic substrate defines the condition under which growth of the microorganism stops completely due, to the absence of the inorganic substrate.

The present invention is also related to a microorganism comprising at least one of the modifications such as described above.

Example I: Construction of Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB (pCC1BAC-serA-serC) (pCL1920-TTadc-CI857-PlambdaR*(−35)-thrA*1-cysE-PgapA-metA*11)

Methionine producing strains with reduced N-acetyl methionine accumulation have been described in patent applications WO2007077041 and WO2009043803 which are incorporated as reference into this application.

1. Construction of the Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB::Km.

To increase the level of phosphoserine phosphatase, SerB, a constitutive artificial trc promoter was added upstream of the serB gene into the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA.

To add this artificial trc promoter, the homologous recombination strategy described by Datsenko & Wanner (2000) was used. This strategy allows the insertion of a kanamycin resistance cassette, but also an additional DNA region, specifically in the chromosome. For this purpose two oligonucleotides, Ptrc07-serBF (SEQ ID No 01) and Ptrc07-serBR (SEQ ID No 02), were used (reference sequence available on the ECOGENE website).

Ptrc07-serBF
(SEQ ID No 01)
CCACCCTTTGAAAATTTGAGACTTAATGTTGCCAGAAGCAATGGATACA

AGGTAGCCTCATGCT<u>CACACTGGCTCACCTTCGGGTGGGCCTTTCTGCC</u>

ATATGAATATCCTCCTTAG with
a region (upper case) homologous to the sequence from 4622816 to 4622878 of the region of the gene serB,
a region (upper underlined case) for T7Te transcriptional terminator sequence from T7 phage (Harrington K. J., Laughlin R. B. and Liang S. Proc Natl Acad Sci USA. 2001 Apr. 24; 98(9):5019-24.),
a region (upper bold case) for the amplification of the kanamycin resistance cassette (reference sequence in Datsenko, K. A. & Wanner, B. L., 2000, PNAS, 97: 6640-6645).

Ptrc07-serBR
(SEQ ID No 02)
CGCACCAGGTAATGTTAGGCATTAAGGCTCCTGTAAAATCGTTCGAAGC

AGGGAAAATAA*CTTCCACACATTATACGAGCCGGATGATTAATCGCCAA*

*CAGCTT*TGTAGGCTGGAGCTGCTTCG with
a region (upper case) homologous to the sequence from 4622939 to 4622879 of the region of the gene serB,
a region (upper italic case) for the trc promoter sequence,
a region (upper bold case) for the amplification of the kanamycin resistance cassette (reference sequence in Datsenko, K. A. & Wanner, B. L., 2000, PNAS, 97: 6640-6645).

The oligonucleotides Ptrc07-serBF (SEQ ID No 01) and Ptrc07-serBR (SEQ ID No 02) were used to amplify the kanamycin resistance cassette from the plasmid pKD4. The obtained PCR product was then introduced by electroporation into the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA (pKD46), in which the expressed Red recombinase enzyme permits the homologous recombination. The kanamycin resistant transformants were then selected, and the insertion of the resistance cassette was verified by a PCR analysis with the oligonucleotides serBF (SEQ ID No 03) and serBR (SEQ ID No 04) defined below. Then the selected transformants were verified by DNA sequencing.

The strain retained was designated MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB::Km.

serBF (SEQ ID No 03)
CAAGGCAAGACAGAACAGG (homologous to the sequence from 4622747 to 4622765 of the region of the gene serB).

serBR (SEQ ID No 04)
GGCATCACTTCATCACCAC (homologous to the sequence from 4623006 to 4622988 of the region of the gene serB).

2. Construction of the Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB Subsequently the kanamycin resistance cassette was eliminated. The pCP20 plasmid, carrying recombinase FLP acting at the FRT sites of the kanamycine resistance cassette, was introduced into the recombinant strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB::Km by electroporation. After a series of cultures at 42° C., the loss of the kanamycin resistance cassette was verified by PCR analysis with the same oligonucleotides as those used previously, serBF (SEQ ID No 03)/serBR (SEQ ID No 04). The strain retained was designated MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB.

3. Construction of the Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB (pCC1BAC-serA-serC)

The construction of the pCC1BAC-serA-serC vector has been described in WO2009043803.

The pCC1BAC-serA-serC vector was introduced by electroporation into the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB giving the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB (pCC1BAC-serA-serC).

4. Construction of the Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB (pCC1BAC-serA-serC) (pCL1920-TTadc-CI857-PlambdaR*(−35)-thrA*1-cysE-PgapA-metA*11)

The pCL1920-TTadc-CI857-PlambdaR*(−35)-thrA*1-cysE-PgapA-metA*11 plasmid is derived from plasmids pCL1920 (Lerner & Inouye, 1990, NAR 18, 15 p 4631), pME101-thrA*1-cysE and pFC1 (Mermet-Bouvier & Chauvat, 1994, Current Microbiology, vol. 28, pp 145-148).

The construction of pME101-thrA*1-cysE was described in WO2007077041.

For the construction of the plasmid pCL1920-TTadc-CI857-PlambdaR*(−35)-thrA*1-cysE-PgapA-metA*11, TTadc-CI857-PlambdaR*(−35)-thrA*1-cysE and PgapA-metA*11 regions were individually obtained by overlapping PCR, then cloned together in the pCL1920 vector.

First, the TTadc-CI857-PlambdaR*(−35) region was PCR amplified from the pFC1 vector by using the following oligonucleotides, ApaI-TTadc-CI857-F-1 (SEQ ID No 05) and PlambdaR-thrA-R-2 (SEQ ID No 06) (reference sequence available on the ECOGENE website and www.genomejp/dbget-bin/www_bfind?*C.acetobutylicum*).Secondly, the thrA*1-cysE region was PCR amplified from the pME101-thrA*1-cysE plasmid using the oligonucleotides PlambdaR-thrA-F-3 (SEQ ID No. 07) and cysE-R-4 (SEQ ID No 08) (reference sequence available on the ECOGENE website). Both Plambda-RthrA-R-2 (SEQ ID No 06) and PlambdaR-thrA-F-3 (SEQ ID No 07) oligonucleotides were designed to possess a 32 bp long overlapping sequence. Owing this overlapping sequence, in a third step, the TTadc-CI857-PlambdaR*(−35)-thrA*1-cysE region was PCR amplified by mixing the TTadc-CI857-PlambdaR*(−35) and thrA*1-cysE PCR products and by using the ApaI-TTadc-CI857-F-1 (SEQ ID No. 05) and cysE-R-4 (SEQ ID No 08) oligonucleotides. Then this PCR product was cloned in the pSCB (Stratagene) and the resulting vector was verified by sequencing and named pSCB-TTadc-CI857-PlambdaR*(−35)-thrA*1-cysE.

ApaI-TTadc-CI857-F-1
(SEQ ID No 05)
accttgccga<u>GGGCCC</u>TAAAAATAAGAGTTACCTTAAATGGTAACTCTT

ATTTTTTTTATCAGCCAAACGTCTCTTCAGGCC with
    a region (lower case) with extra-bases,
    a region (upper underlined case) harbouring the ApaI site,
    a region (upper case) for TTadc transcriptional terminator sequence (transcription terminator of the adc gene from *Clostridium acetobutylicum*, homologous from 179847 to 179807 of the pSLO1 megaplasmid),
    a region (upper bold case) homologous to the 3' extremity of the cI857 gene from lambda bacteriophage.

PlambdaR-thrA-R-2
(SEQ ID No 06)
**CAACACTC*T*** <u>CAT</u>ATGACCTCCTTAGTACATGCAACCATTATCACCGCCA

GAGGTAAAATTGTCAACACGCACGGTGTTAGATATTTATCCCTTGC with
    a region (upper bold case) homologous to the 5' extremity of the thrA gene (from 337 to 348, except for 1 base (upper bold italic case))
    a region (upper case) homologous to the lambda bacteriophage $P_R$ promoter, except 1 base (upper italic case) to obtain the *(−35) version of the $P_R$, variant form in which the −35 box is modified to obtain the −35 consensus (from TTGACT to TTGACA)
    an overlapping region with the PlambdaR-thrA-F-3 oligonucleotide (upper underlined case).

PlambdaR-thrA-F-3
(SEQ ID No 07)
<u>GCATGTACTAAGGAGGTCAT**ATG*A*GAGTGTTGAAGTTCGGCGGTACATC**</u>

AGTGGCAAATGC with
- a region (upper case) homologous to the lambda bacteriophage $P_R$ promoter,
- a region (upper bold case) homologous to the 5' extremity of the thrA gene (from 337 to 377, except for 1 base (upper bold italic case))
- an overlapping region with the PlambdaR-thrA-R-2 oligonucleotide (upper underlined case)

cysE-R-4 (SEQ ID No 08)
AGCTTGCATGCCTGCAGGTCG (homologous to the cysE downstream region of the pME101-thrA*1-cysE plasmid)

To transfer the thrA*1 and cysE genes in a low copy vector, the pSCB-TTadc-CI857-PlambdaR*(−35)-thrA*1-cysE vector was restricted by BsrBI and BamHI and the TTadc-CI857-PlambdaR*(−35)-thrA*1-cysE fragment cloned into the SmaI/BamHI sites of the vector pCL1920, resulting in the vector pCL1920-TTadc-CI857-PlambdaR*(−35)-thrA*1-cysE.

Subsequently, the PgapA-metA*11 region was amplified from the MG1655 metA*11 strain by an overlapping PCR. First, the PgapA promoter was PCR amplified using the oligonucleotides SmaI-PgapA-F (SEQ ID No 09) and PgapA-metA*11-R (SEQ ID No 10) (reference sequence available on the ECOGENE website). Secondly, the metA*11 gene was PCR amplified by using the oligonucleotides PgapA-metA*11-F (SEQ ID No 11) and BamHI-metA*11-R (SEQ ID No 12) (reference sequence available on the ECOGENE website). Both PgapA-metA*11-R (SEQ ID No 10) and PgapA-metA*11-F (SEQ ID No 11) were designed to overlap for their entire sequence. Owing this particularity, in a third step, the PgapA-metA*11 region was PCR amplified by mixing the metA*11 and PgapA PCR products and by using the SmaI-PgapA-F (SEQ ID No 09) and BamHI-metA*11-R (SEQ ID No. 12) oligonucleotides. The PCR product was restricted by SmaI and BamHI, then the digested fragment was blunted in order to clone it into the blunted BamHI site of the vector pCL1920-TTadc-CI857-PlambdaR*(−35)-thrA*1-cysE. The resulting vector was verified by sequencing and named pCL1920-TTadc-CI857-PlambdaR*(−35)-thrA*1-cysE-PgapA-metA*11.

SmaI-PgapA-F
(SEQ ID No 09)
acgt<u>CCCGGG</u>CAAGCCCAAAGGAAGAGTGAGGC with
- a region (lower case) with extra-bases,
- a region (upper underlined case) harbouring the SmaI site,
- a region (upper case) homologous from 1860639 to 1860661 of the PgapA promoter sequence of *Escherichia coli*).

PgapA-metA*11-R
(SEQ ID No 10)
GGCGGGTAGCTCGTCCGGCACACGAATCGGCATATATTCCACCAGCTATTTGTTAGTGAATAAAAGG with
- a region (upper bold case) homologous from 4212335 to 4212303 of the metA gene
- a region (upper case) homologous from 1860794 to 1860761 of the PgapA promoter sequence PgapA-metA*11-F
(SEQ ID No 11)
CCTTTTATTCACTAACAAATAGCTGGTGGAATATATGCCGATTCGTGTGCCGGACGAGCTACCCGCC with
- a region (upper bold case) homologous from 4212335 to 4212303 of the metA gene
- a region (upper case) homologous from 1860794 to 1860761 of the PgapA promoter sequence BamHI-metA*11-R
(SEQ ID No 12)
acgt<u>GGATCC</u>GAATTCCGACTATCACAGAAGATTAATCCAGCGTTGG with
- a region (lower case) with extra-bases,
- a region (upper underlined case) harbouring the BamHI site,
- a region (upper italic case) harbouring the EcoRI site,
- a region (upper bold case) homologous from 4213248 to 4213218 of the metA gene sequence.

Finally, the vector pCL1920-TTadc-CI857-PlambdaR*(−35)-thrA*1-cysE-PgapA-metA*11 was introduced by electroporation into the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB (pCC1BAC-serA-serC) resulting in the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB (pCC1BAC-serA-serC) (pCL1920-TTadc-CI857-PlambdaR*(−35)-thrA*1-cysE-PgapA-metA*11).

5. Evaluation of Temperature Dependent Methionine Production

Strain 1: MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA Ptrc07-serB (pCC1BAC-serA-serC) (pCL1920-TTadc-CI857-PlambdaR*(−35)-thrA*1-cysE-PgapA-metA*11)

Production strains were evaluated in small Erlenmeyer flasks. A 5.5 mL preculture was grown at 30° C. for 21 hours in a mixed medium (10% LB medium (Sigma 25%) with 2.5 g·L$^{-1}$ glucose and 90% minimal medium PC1). It was used to inoculate a 50 mL culture to an OD$_{600}$ of 0.2 in medium PC1. Spectinomycin was added at a concentration of 50 mg·L$^{-1}$, chloramphenicol at 30 mg·L$^{-1}$. The temperature of the culture was either 30° C. or 37° C. When the culture had reached an OD$_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation. For each condition, three repetitions were made.

TABLE 1

| Minimal medium composition (PC1) | |
|---|---|
| Compound | Concentration (g.L$^{-1}$) |
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |

TABLE 1-continued

Minimal medium composition (PC1)

| Compound | Concentration (g.L⁻¹) |
|---|---|
| Citric acid | 6.00 |
| CaCl₂•2H₂O | 0.04 |
| K₂HPO₄•3H₂O | 10.50 |
| Na₂HPO₄ | 2.00 |
| (NH₄)₂HPO₄ | 8.00 |
| NH₄Cl | 0.13 |
| NaOH 4M | Adjusted to pH 6.8 |
| FeSO₄•7H₂O | 0.04 |
| Thiamine | 0.01 |
| Glucose | 10.00 |
| Ammonium thiosulfate | 5.60 |
| Vitamin B12 | 0.01 |
| MOPS | 10.00 |
| IPTG | 0.0024 |

TABLE 2

Methionine yield ($Y_{met}$) in % g methionine/g of glucose produced in batch culture by the strain 1 under different culture conditions. For the definition of methionine/glucose yield see below.

| Condition | $Y_{met}$ | SD | N |
|---|---|---|---|
| Strain 1 - Preculture 30° C. + Culture 30° C. | 10.6 | 0.4 | 3 |
| Strain 1 - Preculture 30° C. + Culture 37° C. | 12.9 | 0.8 | 9 |
| Strain 1 - Preculture 37° C. + Culture 37° C. | 7.4 | 0.9 | 6 |

SD denotes the standard deviation for the yields which was calculated on the basis of several repetitions (N = number of repetitions).

Extracellular methionine concentration was quantified by HPLC after OPA/FMOC derivatization. The residual glucose concentration was analyzed using HPLC with refractometric detection. The methionine yield was expressed as followed:

$$Y_{met} = \frac{\text{methionine}(g)}{\text{consummed glucose}(g)} * 100$$

As shown in table 2 thermo-induction of the expression of genes thrA and cysE during the culture process increases the amount of methionine produced. Constitutive expression throughout the culture process results in low methionine yield.

Table 3 shows that upon induction HDH and SAT activities are increased. Constituve expression of thrA and cysE results in levels of HDH and SAT activity that are between non-induced and induced conditions, explaining in part the lower methionine yield. Other cellular factors most likely impact on these activities upon constituve expression and decrease the activities. In conclusion these results demonstrate that the induction of thrA and cysE is truly beneficial for increasing methionine yield.

TABLE 3

Homoserine dehydrogenase (HDH) and serine acetyltransferase (SAT) activities were determined in the above described cultures and are given in mUI/mg DW.

| condition | HDH | SAT | N |
|---|---|---|---|
| Strain 1 - Preculture 30° C. + Culture 30° C. | 33 ± 0 | 40 ± 12 | 3 |
| Strain 1 - Preculture 30° C. + Culture 37° C. | 94 ± 15 | 246 ± 12 | 3 |
| Strain 1 - Preculture 37° C. + Culture 37° C. | 51 ± 1 | 148 ± 28 | 3 |

Standard deviations were calculated on the basis of several independent cultures (N = number of repetitions).

For the determination of enzyme activities in vitro, E. coli strains were cultured in minimal medium as described above.

Determination of SAT activity has been described in WO 2007077041.

For the determination of HDH activity in vitro, E. coli cells were resuspended in cold 20 mM potassium phosphate buffer (pH7.2) and sonicated on ice (Branson sonifier, 70W). After centrifugation, protein contained in the supernatants was quantified (Bradford, 1976). 10 µL extract (1.5 µg/mL protein) were assayed in 100 mM Tris-HCl pH9, 150 mM KCl, 1 mM NADP⁺ and 25 mM L-Homoserine for 10 minutes at 30° C. NADP⁺ reduction in the presence of L-homoserine is followed spectrophometrically for 30 minutes at 340 nm.

Example II: Construction of Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA DmalS::TTadc-CI857*-PlambdaR03-RBS01-T7RNAPol-TT07::Km (pBeloBAC11-PT7-RBST7-thrA*1-SMC-cysE-PgapA-metA*11-T7TΦ)

Methionine producing strains with reduced N-acetyl methionine accumulation have been described in patent applications WO 2007077041 and WO 2009043803 which are incorporated as reference into this application.

1. Construction of the Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA (pBeloBAC11-PT7-RBST7-thrA*1-SMC-cysE-PgapA-metA*11-T7TΦ)

The plasmid pBeloBAC11-PT7-RBST7-thrA*1-SMC-cysE-PgapA-metA*11-T7TΦ is derived from plasmids pBeloBAC11 (New England BioLabs; Kim et al, 1996, Genomics, 34, 231-218) and pCL1920-TTadc-CI857-PlambdaR*(-35)-thrA*1-cysE-PgapA-metA*11 (described above).

First, thrA*1-SMC-cysE region (SMC for Multiple Clonage Site) was PCR amplified from the pCL1920-TTadc-CI857-PlambdaR*(-35)-thrA*1-cysE-PgapA-metA*11 plasmid by using the following oligonucleotides, SnaBI-thrA-SMC-cysE-F (SEQ ID No 13) and cysE-R(SEQ ID No 14) (reference sequence available on the ECOGENE website).

SnaBI-thrA-SMC-cysE-F (SEQ ID No 13)

tgc*tacgt*accctctcatggaagttaggagtctga*GCTAGCTAGTCCG*

*CTCGAG*ATACGAAAGAAGTCCGCGAACTGG with
- a region (lower case) homologous to the 3' extremity of the thrA gene (from 2765 to 2799) and harbouring the SnaBI restriction site (italic lower case)
- a region (bold case) for SMC region harbouring the NheI and XhoI restriction sites (italic bold case)
- a region (upper case) homologous to the 5' upstream region of cysE gene (from 3780796 to 3780819)

cysE-R (SEQ ID No 14)

CAACCAGTGACCGATGCG homologous to the cysE gene from 3780226 to 3780243

The PCR amplified fragment thrA*1-SMC-cysE was restricted by SnaBI and StuI and the digested fragment was cloned into the SnaBI/StuI sites of the plasmid pCL1920-TTadc-CI857-PlambdaR*(−35)-thrA*1-cysE-PgapA-metA*11. The resulting plasmid was verified by sequencing and named pCL1920-TTadc-CI857-PlambdaR*(−35)-thrA*1-SMC-cysE-PgapA-metA*11.

Subsequently, the PT7-RBST7-thrA*1-SMC-cysE-PgapA-metA*11-T7TΦ region was PCR amplified from pCL1920-TTadc-CI857-PlambdaR*(−35)-thrA*1-cysE-SMC-PgapA-metA*11 plasmid by using the following oligonucleotides, Sfoi-PT7-RBST7-Ndei-thrA-F (SEQ ID No 15) and metA-T7TΦ-SfoI-R (SEQ ID No 16) (reference sequence on the website www.ncbi.nlm.nih.gov/sites/entrez?Db=genome&Cmd=ShowDetailView&TermToSearch=10461&window=7553&begin=21516). This PCR product was cloned into the pSCB vector (Stratagene). The resulting vector was verified by sequencing and named pSCB-PT7-RBST7-thrA*1-SMC-cysE-PgapA-metA*11-T7TΦ. To transfer the PT7-RBST7-thrA*1-SMC-cysE-PgapA-metA*11-T7TΦ region into the single-copy vector pBeloBAC11, the pSCB-PT7-RBST7-thrA*1-SMC-cysE-PgapA-metA*11-T7(1) was restricted by SfoI and the PT7-RBST7-thrA*1-SMC-cysE-PgapA-metA*11-T7TΦ fragment was cloned into the blunted NotI site of the vector pBeloBAC11, resulting in the plasmid pBeloBAC11-PT7-RBST7-thrA*1-SMC-cysE-PgapA-metA*11-T7TΦ.

```
SfoI-PT7-RBST7-NdeI-thrA-F
                                       (SEQ ID No 15)
GGCGCCtcgattcgaacttctgatagacttcgaaattaatacgactcac tatagggagaccacaacggtttccctctagaaataattttgtttaactt taagaaggagatatacatATGAGAGTGTTGAAGTTCGGCGG
``` with
- a region (italic upper case) harbouring the SfoI restriction site
- a region (lower case) homologous to the promoter region of the T7p45 (10A) gene of the T7 bacteriophage (from 22858 to 22967)
- a region (upper bold case) homologous to the thrA gene (from 337 to 359, except for 1 base (upper bold underlined case))

```
metA-T7TΦ-SfoI-R
                                       (SEQ ID No 16)
GGCGCCctttcagcaaaaaaccctcaagacccgtttagaggccccaa ggggttatgctagttattgctcagcggtggcagcagccaactcagctt cctttcgggctttgttagTTAATCCAGCGTTGGATTCATGTGC
``` with
- a region (italic upper case) harbouring the SfoI restriction site
- a region (lower case) homologous to the transcriptional terminator region of the T7p45 (10A) gene of the T7 bacteriophage (from 24111 to 24218)
- a region (upper bold case) homologous to metA gene (from 4213208 to 4213232)

Finally, the plasmid pBeloBAC11-PT7-RBST7-thrA*1-SMC-cysE-PgapA-metA*11-T7TΦ was introduced by electroporation into the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA resulting in the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA (pBeloBAC11-PT7-RBST7-thrA*1-SMC-cysE-PgapA-metA*11-T7TΦ).

2. Construction of the Strain MG1655 metA*11 DmalS::TTadc-CI857*-PlambdaR03-RBS01-T7RNAPol-TT07::Km (pKD46)

To delete the malS region and replace it by TTadc-CI857*-PlambdaR03-RBS01-T7RNAPol-TT07 region, the homologous recombination strategy described by Datsenko & Wanner (2000) was used. This strategy allows the insertion of a kanamycine resistance cassette and additional DNA, while deleting most of the region concerned. For this purpose, the following plasmid was constructed, pUC18-DmalS::TTadc-CI857*-PlambdaR03-RBS01-T7RNAPol-TT07::Km.

The pUC18-DmalS::TTadc-CI857*-PlambdaR03-RBS01-T7RNAPol-TT07::Km plasmid is derived from plasmids pUC18 (Norrander et al., 1983, Gene 26, 101-106) and pUC18-DmalS::SMC::Km (described above), pAR1219 (Sigma), and pCR4BluntTOPO-TTadc-CI857*-PlambdaR*(−35)-RBS01-SMC-TT07 (synthesized by Geneart and described below).

2.1. Construction of the Plasmid pUC18-DmalS::SMC::Km

For the construction of the plasmid pUC18-DmalS::SMC::Km, the upstream region of malS (upmalS), the multiple cloning site (SMC) and the kanamycine cassette (Km) were obtained by overlapping PCR, and the downstream region of malS (downmalS) was amplified and cloned subsequently.

First, the upmalS region was PCR amplified from the MG1655 E. coli genomic DNA using the following oligonucleotides, HindIII-upmalS-F-1 (SEQ ID No 17) and upmalS-Km-R-2 (SEQ ID No 18) (reference sequence available on the ECOGENE website). Secondly, the KmSMC region was PCR amplified from pKD4 plasmid (Datsenko & Wanner, 2000) using the oligonucleotides upmalS-Km-F-3 (SEQ ID No 19) and Km-SMC-R-4 (SEQ ID No 20). Both upmalS-Km-R-2 (SEQ ID No 18) and upmalS-Km-F-3 (SEQ ID No 19) oligonucleotides were designed to possess 45 bp long overlapping sequence. Owing this overlapping sequence, in a third step, the upmalS-Km-SMC region was PCR amplified by mixing the upmalS and Km-SMC PCR products and by using the Hindiii-upmalS-F-1 (SEQ ID No 17) and Km-SMC-R-4 (SEQ ID No 20) oligonucleotides. Then this PCR product was cloned in the pSCB (Stratagene) and the resulting plasmid was verified by sequencing and named pSCB-upmalS-Km-SMC.

```
HindIII-upmalS-F-1
                                       (SEQ ID No 17)
atcgtaAAGCTTTTCACTTTACCTGGCGCATTGG
``` with
- a region (lower case) with extra-bases
- a region (upper italic case) harbouring the HindIII restriction site
- a region (upper case) homologous to the upstream region of the malS gene (from 3734620 to 3734641)

```
upmalS-Km-R-2
                                       (SEQ ID No 18)
ctaaggaggatattcatatgACCGGTTCGGCGGCGTTCTGGATGG
``` with
- a region (lower case) for the amplification of the kanamycin resistance cassette (reference sequence in Datsenko & Wanner, 2000, PNAS, 97, 6640-6645)
- a region (upper case) homologous to the upstream region of malS gene (from 3735836 to 3735860)

```
upmalS-Km-F-3
                                          (SEQ ID No 19)
CCATCCAGAACGCCGCCGAACCGGTcatatgaatatcctccttag
``` with
- a region (upper case) homologous to the upstream region of the malS gene (from 3735836 to 3735860)
- a region (lower case) for the amplification of the kanamycin resistance cassette (reference sequence in Datsenko & Wanner, 2000, PNAS, 97, 6640-6645)

```
Km-SMC-R-4
                                          (SEQ ID No 20)
GATCGATGGATCCATCTCGAGATCCGCGGATGTATACATGGGCCCtgta ggctggagctgcttcg
``` with
- a region (upper case) with extra-bases
- a region (italic upper case) for the SMC habouring BamHI, XhoI, SacII, BstZ17I, ApaI restriction sites
- a region (lower case) for the amplification of the kanamycin resistance cassette (reference sequence in Datsenko & Wanner, 2000, PNAS, 97, 6640-6645).

Then, the pSCB-upmalS-Km-SMC plasmid was restricted by BamHI and HindIII and the upmalS-Km-SMC fragment was cloned into the BamHI/HindIII sites of the vector pUC18, resulting in the vector pUC18-upmalS-Km-SMC.

Subsequently, the downmalS region was PCR amplified from the MG1655 *E. coli* genomic DNA using the following oligonucleotides, downmalS-F-1 (SEQ ID No 21) and downmalS-R-2 (SEQ ID NO 22) (reference sequence available on the ECOGENE website). Then this PCR product was cloned into the pSCB (Stratagene) and the resulting plasmid was verified by sequencing and named pSCB-downmalS.

```
downmalS-F-1
                                          (SEQ ID No 21)
ATGCTGAATTCaccggtgaagcctggggccacggcg
``` with
- a region (upper case) with extra-bases
- a region (italic upper case) harbouring the EcoRI restriction site
- a region (lower case) homologous to the downstream region of the malS gene (from 3737020 to 3737044)

```
downmalS-R-2
                                          (SEQ ID NO 22)
TACGATGAATTCgggacgccataagcgttatcaatcacc
``` with
- a region (upper case) with extra-bases
- a region (italic upper case) harbouring the EcoRI restriction site
- a region (lower case) homologous to the downstream region of the malS gene (from 3738372 to 3738398).

Then, the pSCB-downmalS plasmid was restricted by EcoRI and the downmalS fragment was cloned into the EcoRI site of the vector pUC18, resulting in the vector pUC18-DmalS::SMC::Km.

2.2. Construction of the Plasmid pUC18-DmalS::TTadc-CI857*-PlambdaR03-RBS01-T7RNAPol-TT07::Km For the construction of the plasmid pUC18-DmalS::TTadc-CI857-PlambdaR03-RBS01-T7RNAPol-TT07::Km, the TTadc-CI857*-PlambdaR*(−35)-RBS01-SMC-TT07 region (described below) present into the pCR4BluntTOPO-TTadc-CI857PlambdaR*(−35)-RBS01-SMC-TT07 (synthesized by Geneart) was restricted by ApaI and BamHI and the fragment was subcloned into the ApaI and BamHI restriction sites of the plasmid pUC18-DmalS::SMC::Km, giving the plasmid pUC18-DmalS::TTadc-CI857PlambdaR*(−35)-RBS01-SMC-TT07::Km. Then the PlambdaR03-RBS01-T7RNApol-TT07 region was amplified from the vector pAR1219 (Sigma) using the following oligonucleotides, AvrII-PlambdaR03-RBS01-T7RNApol-F (SEQ ID No 24) and T7RNApol-BstZ17I-TT07-BamHI-Xhoi-R(SEQ ID No 25) (reference sequence available on the ECOGENE website and www.ncbi.nlm.nih.gov/sites/entrez?Db=genome&Cmd=ShowDetailView&TermToSearch=10461&window=7553&begin=21516). Then the PCR product was restricted by AvrII and BamHI and the fragment was cloned into the partially AvrII and BamHI restricted pUC18-DmalS::TTadc-CI857-PlambdaR*(−35)-RBS01-SMC-TT07::Km plasmid, giving the pUC18-DmalS::TTadc-CI857-PlambdaR03-RBS01-T7RNApolTT07::Km plasmid which was verified by DNA sequencing.

TTadc-CI857*-PlambdaR*(−35)-RBS01-SMC-TT07 region present into the pCR4BluntTOPO-TTadc-CI857*-PlambdaR*(−35)-RBS01-SMC-TT07 (SEQ ID No 23):

```
gggcccTAAAAATAAGAGTTACCTTAAATGGTAACTCTTATTTTTTTA ttaattaacctaggTCAGCCAAACGTCTCTTCAGGCCACTGACTAGCGA

TAACTTTCCCCACAACGGAACAACTCTCATTGCATGGGATCATTGGGTA

CTGTGGGTTTAGTGGTTGTAAAAACACCTGACCGCTATCCCTGATCAGT

TTCTTGAAGGTAAACTCATCACCCCCAAGTCTGGCTATGCAGAAATCAC

CTGGCTCAACAGCCTGCTCAGGGTCAACGAGAATTAACATTCCGTCAGG

AAAGCTTGGCTTGGAGCCTGTTGGTGCGGTCATGGAATTACCTTCAACC

TCAAGCCAGAATGCAGAATCACTGGCTTTTTTGGTTGTGCTTACCCATC

TCTCCGCATCACCTTTGGTAAAGGTTCTAAGCTTAGGTGAGAACATCCC

TGCCTGAACATGAGAAAAACAGGGTACTCATACTCACTTCTAAGTGAC

GGCTGCATGCTAACCGCTTCATACATCTCGTAGATTTCTCTGGCGATTG

AAGGGCTAAATTCTTCAACGCTAACTTTGAGAATTTTTGTAAGCAATGC

GGCGTTGTAAGCATTTAATGCATTGATGCCATTAAATAAAGCACCAACG

CCTGACTGCCCCATCCCCATCTTGTCTGCGACAGATTCCTGGGATAAGC

CAAGTTCATTTTTCTTTTTTTCATAAATTGCCTTAAGGCGACGTGCGTC

CTCAAGCTGCTCTTGTGTTAATGGTTTCTTTTTTGTGCTCATcctaggA

ATCTATCACCGCAAGGGATAAATATCTAACACCGTGCGTGTTGACAATT

TTACCTCTGGCGGTGATAATGGTTGCATGTACTAAGGAGGTTATAAGTA

TACtcacactggctcaccttcgggtgggcctttctgcggatcc
``` with
- regions (italic lower case) harbouring the restriction sites ApaI, PacI, AvrII and BamHI
- a region (underlined upper case) homologous to the TTadc transcriptional terminator sequence (transcription terminator of the adc gene from *Clostridium acetobutylicum*, homologous from 179847 to 179807 of the pSLO1 megaplasmid) (TTadc)
- a region (upper case) homologous to the cI857 gene harbouring codon usage changes in aim to create or to delete some restriction sites (italic upper case) (CI857*)
- a region (bold upper case) homologous to the lambda bacteriophage $P_R$ promoter, except 1 base (italic bold upper case) to obtain the *(−35) version of the $P_R$, variant form in which the −35 box is modified to obtain the −35 consensus (from TTGACT to TTGACA) (PlambdaR*(−35))
- a region (underlined bold upper case) for ribosome biding site (RBS01)
- a region (underlined italic upper case) harbouring BstZ17I restriction site (SMC)
- a region (underlined lower case) for T7Te transcriptional terminator sequence (Harrington et al., 2001, PNAS, 98(9), 5019-24) (TT07)

```
AvrII-PlambdaR03-RBS01-T7RNApol-F
                                    (SEQ ID No 24)
ctcatCCTAGGAATCTATCACCGCAAGGGATAAATATCTAACACCGTGC
GTGTTGATCATTTTACCTCTGGCGGTGATAATGGTTGCATGTACTAAG
GAGGTTATAAatgaacacgattaacatcgctaagaacg
``` with
- a region (lower case) with extrabases
- a region (italic upper case) harbouring the AvrII restriction site
- a region (bold upper case) homologous to the lambda bacteriophage $P_R$ promoter, except 2 bases (italic bold upper case) to obtain the PlambdaR03 mutant version of the $P_R$ promoter
- a ribosome binding site (underlined upper case)
- a region (bold lower case) homologous to the 5' extremity of the bacteriophage T7 RNA polymerase gene (T7p07 gene) (from 3171 to 3198)

```
T7RNApol-BstZ17I-TT07-BamHI-XhoI-R
                                    (SEQ ID No 25)
cggccagCTCGAGCGCGGATCCGCAGAAAGGCCCACCCGAAGGTGAGCC
AGTGTGAGTATACttacgcgaacgcgaagtccgac
``` with
- a region (lower case) with extra-bases
- a region (italic upper case) harbouring the XhoI and BamHI restriction sites
- a region (bold upper case) for T7Te transcriptional terminator sequence (Harrington et al., 2001, PNAS, 98(9), 5019-24)
- a region (underlined italic upper case) harbouring the BstZ17I restriction site
- a region (bold lower case) homologous to the 3' extremity of the bacteriophage T7 RNA polymerase gene (T7p07 gene) (from 5801 to 5822).

2.3. Replacement of the malS Region by TTadc-CI857*-PlambdaR03-RBS01-T7RNAPol-TT07 Region Finally, in order to delete the malS region and replace it by TTadc-CI857*-PlambdaR03-RBS01-T7RNAPol-TT07 region, the pUC18-DmalS::TTadc-CI857-PlambdaR03-RBS01-T7RNApol-TT07::Km plasmid was restricted by Scat and EcoRV and the DmalS::TTadc-CI857-PlambdaR03-RBS01-T7RNApol-TT07::Km fragment was introduced by electroporation into the strain MG1655 metA*11 (pKD46), in which the expressed Red recombinase enzyme permits the homologous recombination. The kanamycin resistant transformants were then selected, and the insertion of the DmalS::TTadc-CI857*-PlambdaR03-RBS01-T7RNApol-TT07::Km fragment was verified by a PCR analysis with the oligonucleotides malS-F (SEQ ID No. 26), Km-R (SEQ ID No 27), T7RNApol-F (SEQ ID No 28) and malS-R (SEQ ID No 29) (reference sequence available on the ECOGENE website and on the National Center for Biotechnology Information (NCBI) website). The strain is designated MG1655 metA*11 DmalS::TTadc-CI857*PlambdaR03-RBS01-T7RNApol-TT07::Km.

malS-F (SEQ ID No 26): GCACCAACAACGCTTCAGGC (homologous to the malS region from 3734280 to 3734299)

Km-R (SEQ ID No 27): TGTAGGCTGGAGCTGCTTCG (homologous to the kanamycin resistance cassette of the pKD4 vector)

T7RNApol-F (SEQ ID No 28): GCTGCTAAGCTGCTG-GCTGC (homologous to the bacteriophage T7 RNA polymerase gene (T7p07 gene) from 5274 to 5293)

malS-R (SEQ ID NO 29): GGAAAGACTCATGCACAGC (homologous to the malS region from 3738453 to 3738471.

3. Construction of the Strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA DmalS::TTadc-CI857*-PlambdaR03-RBS01-T7RNAPol-TT07::Km (pBeloBAC11-PT7-RBST7-thrA*1-SMC-cysE-PgapA-metA*11-T7TΦ)

To delete the malS region and replace it by the TTadc-CI857*-PlambdaR03-RBS01-T7RNAPol-TT07 region in the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA (pBeloBAC11-PT7-RBST7-thrA*1-SMC-cysE-PgapA-metA*11-T7TΦ), the DmalS::TTadc-CI857*-PlambdaR03-RBS01-T7RNApol-TT07::Km construction was transferred by P1 phage transduction (see below) from the MG1655 metA*11 DmalS::TTadc-CI857*-PlambdaR03-RBS01-T7RNApol-TT07:: Km strain into the MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA (pBeloBAC11-PT7-RBST7-thrA*1-SMC-cysE-PgapA-metA*11-T7TΦ) strain. Kanamycin and chloramphenicol resistant transformants were selected and the insertion of the DmalS::TTadc-CI857*-PlambdaR03-RBS01-T7RNApol-TT07::Km region was verified by a PCR analysis with the oligonucleotides malS-F (SEQ ID No 26), Km-R (SEQ ID No 27), T7RNApol-F (SEQ ID No 28) and malS-R (SEQ ID No 29) previously described. The strain retained is designated MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA DmalS::TTadc-CI857*-PlambdaR03-RBS01-T7RNApol-TT07::Km (pBeloBAC11-PT7-RBST7-thrA*1-SMC-cysE-PgapA-metA*11-T7TΦ).

Preparation of Phage Lysate P1:
- Inoculation with 100 μL of an overnight culture of the strain MG1655 metA*11 DmalS::TTadc-CI857*-PlambdaR03-RBS01-T7RNApol-TT07::Km of 10 mL of LB supplemented with kanamycine (50 μg/mL), glucose (0.2%) and $CaCl_2$ (5 mM)
- Incubation for 1 h at 30° C. with shacking
- Addition of 100 μL of phage lysate P1 prepared on the strain MG1655 (about $1 \cdot 10^9$ phage/mL)
- Shacking at 30° C. for 3 hours until all cells were lysed
- Addition of 200 μL of chlorophorm and vortexing Centrifugation for 10 min at 4500 g to eliminate cell debris
Transfer of the supernatant to sterile tube and addition of 200 µl of chloroform
Storage of lysate at 4° C.
Transduction:
Centrifugation for 10 min at 1500 g for 5 mL of an overnight culture of the strain MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA (pBeloBAC11-PT7-RBST7-thrA*1-SMC-cysE-PgapA-metA*11-T7TΦ) in LB medium
Suspension of the cell pellet in 2.5 mL of 10 mM of MgSO$_4$, 5 mM CaCl$_2$
Control tubes:
  100 µl of cells
  100 µl phages P1 of strain MG1655 metA*11 DmalS::TTadc-CI857*-PlambdaR03-RBS01-T7RNApol-TT07::Km
Test tubes: 100 µl of cells+100 µL phages P1 of strain MG1655 metA*11 DmalS::TTadc-CI857*-PlambdaR03-RBS01-T7RNApol-TT07::Km
Incubation for 30 min at 30° C. without shacking
Addition of 100 µl of 1 M sodium citrate in each tube and vortexing
Addition of 1 mL of LB
Incubation for 1 hour at 30° C. with shacking
Spreading on dishes LB supplemented with kanamycine (50 µg/mL) after centrifuging of tubes for 3 min at 7000 rpm
Incubation at 30° C. overnight 4. Evaluation of Temperature Dependent Methionine Production Strain 2: MG1655 metA*11 Ptrc-metH PtrcF-cysPUWAM PtrcF-cysJIH Ptrc09-gcvTHP Ptrc36-ARNmst17-metF DmetJ DpykF DpykA DpurU DyncA DmalS::TTadc-CI857*-PlambdaR03-RBS01-T7RNApol-TT07::Km (pBeloBAC11-PT7-RBST7-thrA*1-SMC-cysE-PgapA-metA*11-T7TΦ)

Preculture and culture conditions are described above in example 1. Kanamycin was used instead of spectinomycine. The temperature of culture was either 30° C. or 34° C.

TABLE 4

Methionine yield ($Y_{met}$) in % g methionine/g de glucose produced in batch culture by the strain 2 at 30 and 34° C. For the precise definition of methionine/glucose yield see above.

| Condition | $Y_{met}$ | SD | N |
|---|---|---|---|
| Strain 2 - Preculture 30° C. + Culture 30° C. | 6.7 | 0.1 | 3 |
| Strain 2 - Preculture 30° C. + Culture 34° C. | 9.9 | 0.4 | 3 |

SD denotes the standard deviation for the yields which was calculated on the basis of three repetitions.

Induction of thrA and cysE increases the amount of methionine produced. This is confirmed by an analysis of the two activities HDH and SAT. Both activities increase upon the shift to 34° C.

TABLE 5

Homoserine dehydrogenase (HDH, thrA*1) and serine acetyltransferase (SAT, cysE) activities were determined in the above described cultures and were given in mUI/mg of proteins.

| condition | HDH | SAT | N |
|---|---|---|---|
| Strain 2 - Preculture 30° C. + Culture 30° C. | 58.9 ± 2.8 | 77.0 ± 8.3 | 3 |

TABLE 5-continued

Homoserine dehydrogenase (HDH, thrA*1) and serine acetyltransferase (SAT, cysE) activities were determined in the above described cultures and were given in mUI/mg of proteins.

| condition | HDH | SAT | N |
|---|---|---|---|
| Strain 2 - Preculture 30° C. + Culture 34° C. | 91.7 ± 4.4 | 131.0 ± 9.7 | 3 |

Standard deviations were calculated on the basis of several independent cultures (N = number of repetitions).

Example III: Constructions of the Thermo-Inducible Strains Tested in Examples IV and V Below 1. Protocols Several protocols have been used to construct methionine producing strains and are described in the following examples.

Protocol 1:

Chromosomal Modifications by Homologous Recombination and Selection of Recombinants (Datsenko, K. A. & Wanner, B. L., 2000)

Allelic replacement or gene disruption in specified chromosomal loci was carried out by homologous recombination as described by Datsenko. & Wanner (2000). The chloramphenicol (Cm) resistance cat, the kanamycin (Km) resistance kan, the gentamycin (Gt) resistance gm genes or tetracycline (Tc) resistance tet, flanked by Flp recognition sites, were amplified by PCR by using pKD3 or pKD4, p34S-Gm (Dennis et Zyltra, AEM July 1998, p 2710-2715) or pLOI2065 (Underwood et al., Appl Environ Microbiol. 2002 December; 68(12): 6263-6272) plasmids as template respectively. The resulting PCR products were used to transform the recipient E. coli strain harbouring plasmid pKD46 that expresses the λ Red (γ, β, exo) recombinase. Antibiotic-resistant transformants were then selected and the chromosomal structure of the mutated loci was verified by PCR analysis with the appropriate primers listed in Table 2.

The cat, kan, gm and α-resistance genes were removed by using plasmid pCP20 as described by Datsenko. & Wanner (2000), except that clones harboring the pCP20 plasmid were cultivated at 37° C. on LB and then tested for loss of antibiotic resistance at 30° C. Antibiotic sensitive clones were then verified by PCR using primers listed in Table 2.

Protocol 2:

Transduction of Phage P1

Chromosomal modifications were transferred to a given E. coli recipient strain by P1 transduction. The protocol is composed of 2 steps: (i) preparation of the phage lysate on a donor strain containing the resistance associated chromosomal modification and (ii) infection of the recipient strain by this phage lysate.

Preparation of the Phage Lysate

Inoculate 100 µl of an overnight culture of the strain MG1655 with the chromosomal modification of interest in 10 ml of LB+Cm 30 µg/ml or Km 50 µg/ml or Gt 10 µg/mL or Tet 10 µg/mL+glucose 0.2%+CaCl$_2$ 5 mM.
Incubate 30 min at 37° C. with shaking.
Add 100 µl of P1 phage lysate prepared on the donor strain MG1655 (approx. 1×10$^9$ phage/ml).
Shake at 37° C. for 3 hours until the complete lysis of cells.
Add 200 µl of chloroform, and vortex
Centrifuge 10 min at 4500 g to eliminate cell debris.

Transfer of supernatant to a sterile tube.
Store the lysate at 4° C.
Transduction
Centrifuge 10 min at 1500 g 5 ml of an overnight culture of the E. coli recipient strain cultivated in LB medium.
Suspend the cell pellet in 2.5 ml of MgSO4 10 mM, CaCl2 5 mM.
Infect 100 µl cells with 100 µl P1 phage of strain MG1655 with the modification on the chromosome (test tube) and as a control tubes 100 µl cells without P1 phage and 100 µl P1 phage without cells.
Incubate 30 min at 30° C. without shaking.
Add 100 µl sodium citrate 1 M in each tube, and vortex.
Add 1 ml of LB.
Incubate 1 hour at 37° C. with shaking
Centrifuge 3 min at 7000 rpm.
Plate on LB+Cm 30 µg/ml or Km 50 µg/ml or Gt 10 µg/mL or Tet 10 µg/mL
Incubate at 37° C. overnight.

The antibiotic-resistant transductants were then selected and the chromosomal structure of the mutated locus was verified by PCR analysis with the appropriate primers listed in Table 2.

thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11

Methionine producing strain 3 (Table 6) has been described in patent applications EP10306164.4 and U.S. 61/406,249. These applications are incorporated as reference into this application.

2. Construction of Strain 4: MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11::Cm The ΔwcaM::TT02-TTadc-PlambdaR*(−35)-RBS01-thrA*1-cysE-PgapA-metA*11::Cm chromosomal modification, described in patent applications EP10306164.4 and U.S. 61/406,249 was transduced into the strain 3 (Table 6) with a P1 phage lysate from strain MG1655 metA*11

TABLE 6

List of genotypes and corresponding numbers of intermediate strains and producer strains that appear in the following examples.

| Strain Number | Genotype |
|---|---|
| 3 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 |
| 4 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1*-cysE-PgapA-metA*11 ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11::Cm |
| 5 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1*-cysE-PgapA-metA*11 ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11::Cm ΔyjbI::TT02-TTadc-PlambdaR*(-35)-RBS01-thrA*1-cysE-PgapA-metA*11::Tc |
| 6 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1*-cysE-PgapA-metA*11 ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11::Cm ΔyjbI::TT02-TTadc-PlambdaR*(-35)-RBS01-thrA*1-cysE-PgapA-metA*11::Tc ΔmelB::TT02-TTadc-PlambdaR*(-35)-RBS01-thrA*1-cysE-PgapA-metA*11::Gt |
| 7 | MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-PlambdaR*(-35)-thrA*1-cysE |
| 8 | MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-PlambdaR*(-35)-thrA*1-cysE pBeloBAC11-PL1*1/RBS01*2-thrA*1-SMC-cysE-PgapA-metA*11-T7TΦ |

1. Construction of Strain 3: MG1655 metA*11 Ptrc-metH PtrcF-cysPUWAM PtrcF-cysJIH Ptrc09-gcvTHP Ptrc36-ARNmst-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01- pKD46 ΔwcaM::TT02-TTadc-PlambdaR*(−35)-RBS01-thrA*1-cysE-PgapA-metA*11::Cm described in patent applications EP10306164.4 and U.S. 61/406,249, according to Protocol 2.

Chloramphenicol resistant transductants were selected and the presence of the ΔwcaM::TT02-TTadc-PlambdaR*(−35)-RBS01-thrA*1-cysE-PgapA-metA*11::Cm chromosomal modification was verified by PCR with Ome1707-DwcaM_verif_F (SEQ ID No 30) and Ome1708-DwcaM_verif_R (SEQ ID No 31) (Table 7). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11::Cm was called strain 4 (Table 1).

3. Construction of Strain 5: MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA A malS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11::Cm ΔyjbI::TT02-TTadc-PlambdaR*(−35)-RBS01-thrA*1-cysE-PgapA-metA*11::Tc 3.1. Construction of Plasmid pUC18-TTadc-CI*0-PlambdaR*(−35)-ΔyjbI::TT02-TTadc-PlambdaR*(−35)-RBS01-thrA*1-cysE-PgapA-metA*11::Tc Plasmid pUC18-TTadc-CI*0-PlambdaR*(−35)-ΔyjbI::TT02-TTadc-PlambdaR*(−35)-RBS01-thrA*1-cysE-PgapA-metA*11::Tc is derived from plasmids pUC18-TTadc-CI*0-PlambdaR*(−35)-ΔpgaABCD::TT02-TTadc-PlambdaR*(−35)-RBS01-thrA*1-cysE-PgapA-metA*11::Tc and pUC18-TTadc-CI*0-PlambdaR*(−35)-ΔyjbI::TT02-SMC described above, pMA-RQ-TTadc-CI*0-PlambdaR*(−35)-RBS01*2 described below and pLOI2065 (Underwood et al., Appl Environ Microbiol. 2002 December; 68(12): 6263-6272).

3.1.1. Construction of pUC18-TTadc-CI*0-PlambdaR*(−35)-ΔpgaABCD::TT02-TTadc-PlambdaR*(−35)-RBS01-thrA*1-cysE-PgapA-metA*11::Tc Plasmid pUC18-TTadc-CI*0-PlambdaR*(−35)-ΔpgaABCD::TT02-TTadc-PlambdaR*(−35)-RBS01-thrA*1-cysE-PgapA-metA*11::Tc plasmid is derived from pMA-RQ-TTadc-CI*0-PlambdaR*(−35)-RBS01*2 describe above, pLOI2065 (Underwood et al., Appl Environ Microbiol. 2002 December; 68(12): 6263-6272) and pUC18-ΔpgaABCD::TT02-TTadc-PlambdaR*(−35)-RBS01-thrA*1-cysE-PgapA-metA*11::Cm described in EP10306164.4 and U.S. 61/406,249 patent applications.

Construction of Plasmid pMA-RQ-TTadc-CI*0-PlambdaR*(−35)-RBS01*2 pMA-RQ-TTadc-CI*0-PlambdaR*(−35)-RBSOI*2 is derived from plasmids pMA-RQ-TTadc-CI*1-PlambdaR*(−35)-RBS01*2 and pMA-RQ-TTadc-CI*3-PlambdaR*(−35)RBS01*2 which have been synthesized by GeneArt (www.geneart.com/). The TTadc-CI*1-PlambdaR*(−35)-RBS01*2 and TTadc-CI*3-PlambdaR*(−35)-RBS01*2 fragments were cloned into the SfiI sites of plasmid pMA-RQ from GeneArt and contain the following sequences respectively:

pMA-RQ-TTadc-CI*1-PlambdaR*(−35)-RBS01*2
(SEQ ID No 32)
ggccgtcaaggccgcatggcgcgccttataacctccttaGTACATGCAA
CCATTATCACCGCCAGAGGTAAAATTGTCAACACGCACGGTGTTAGATA
TTTATCCCTTGCGGTGATAGATTTAACGTATGAGCACAAAAAAGAAACC
ATTAACACAAGAGCAGCTTGAGGACGCACGTCGCCTTAAGGCAATTCAT
GAAAAAAGAAAAATGAACTTGGCTTATCCCAGGAATCTGTCGCAGACA
AGATGGGGATGGGGCAGTCAGGCGTTGGTGCTTTATTTAATGGCATCAA
TGCATTAAATGCTTACAACGCCGCATTGCTTGCGAAAATTCTCAAAGTT
AGCGTTGAAGAATTTAGCCCTTCAATCGCCAGAGAAATCTACGAGATGT
ATGAAGCGGTTAGCATGCAGCCGTCACTTAGAAGTGAGTATGAGTACCC
TGTTTTTTCTCATGTTCAGGCAGGGATGTTCTCACCTGAACTTAGAACC
TTTACCAAGGTGATGCGGAGAGATGGGTAAGCACAACCAAAAAAGCCA
GTGATTCTGCATTCTGGCTTGAGGTTGAAGGTAATTCCATGACCGCACC
AACAGGCTCCAAGCCAAGCTTTCCTGACGGAATGTTAATTCTCGTTGAC
CCTGAGCAGGCTGTTGAGCCAGGTGATTTCTGCATAGCCAGACTTGGGG
GTGATGAGTTTACCTTCAAGAAACTGATCAGGGATAGCGGTCAGGTGTT
TTTACAACCACTAAACCCACAGTACCCAATGATCCCATGCAATGAGAGT
TGTTCCGTTGTGGGGAAAGTTATCGCTAGTCAGTGGCCTGAAGAGACGT
TTGGCTGA**TAAAAAAAATAAGAGTTACCATTTAAGGTAACTCTTATTTT
TA**GGGCCCTTAATTAACTGGGCCTCATGGGCC

- underline lower cases corresponding to SfiI and AscI restriction sites
- bold lower cases corresponding to RBS01*2 sequences (TAAGGAGGTTATAA) in reverse orientation and PsiI restriction site,
- italic upper cases homologous to lambda bacteriophage P$_R$ promoter (PlambdaR*(−35), (Mermet-Bouvier & Chauvat, 1994, Current Microbiology, vol. 28, pp 145-148)).
- upper cases corresponding to the sequence of the repressor protein cI of the lambda bacteriophage where the nucleotide T67 were changed by C67 generating one amino-acid change Tyr23His (Mermet-Bouvier & Chauvat, 1994, Current Microbiology, vol. 28, pp 145-148). This sequence was called cI*1.
- bold upper cases homologous to TTadc transcriptional terminator sequence in revser orientation (transcription terminator of the adc gene from Clostridium acetobutylicum, homologous from 179847 to 179807 of the pSLO1 megaplasmid).
- underlined upper cases corresponding to ApaI, PacI and SfiI pMA-RQ-TTadc-CI*3-PlambdaR*(−35)-RBS01*2
(SEQ ID No 33)
ggccgtcaaggccgcatggcgcgccttataacctccttaGTACATGCAA
CCATTATCACCGCCAGAGGTAAAATTGTCAACACGCACGGTGTTAGATA
TTTATCCCTTGCGGTGATAGATTTAACGTATGAGCACAAAAAAGAAACC
ATTAACACAAGAGCAGCTTGAGGACGCACGTCGCCTTAAGGCAATTTAT
GAAAAAAGAAAAATGAACTTGGCTTATCCCAGGAATCTGTCGCAGACA -continued

```
AGATGGGGATGGGGCAGTCAGGCGTTGGTGCTTTATTTAATGGCATCAA

TGCATTAAATGCTTACAACGCCGCATTGGCGACAAAAATTCTCAAAGTT

AGCGTTGAAGAATTTAGCCCTTCAATCGCCAGAGAAATCTACGAGATGT

ATGAAGCGGTTAGCATGCAGCCGTCACTTAGAAGTGAGTATGAGTACCC

TGTTTTTTCTCATGTTCAGGCAGGGATGTTCTCACCTAAGCTTAGAACC

TTTACCAAAGGTGATGCGGAGAGATGGGTAAGCACAACCAAAAAAGCCA

GTGATTCTGCATTCTGGCTTGAGGTTGAAGGTAATTCCATGACCGCACC

AACAGGCTCCAAGCCAAGCTTTCCTGACGGAATGTTAATTCTCGTTGAC

CCTGAGCAGGCTGTTGAGCCAGGTGATTTCTGCATAGCCAGACTTGGGG

GTGATGAGTTTACCTTCAAGAAACTGATCAGGGATAGCGGTCAGGTGTT

TTTACAACCACTAAACCCACAGTACCCAATGATCCCATGCAATGAGAGT

TGTTCCGTTGTGGGGAAAGTTATCGCTAGTCAGTGGCCTGAAGAGACGT

TTGGCTGATAAAAAAAATAAGAGTTACCATTTAAGGTAACTCTTATTTT

TAGGGCCCTTAATTAACTGGGCCTCATGGCC
```

- underline lower cases corresponding to SfiI and AscI restriction sites
- bold lower cases corresponding to RBS01*2 sequences (TAAGGAGGTTATAA) in reverse orientation and PsiI restriction site,
- italic upper cases homologous to lambda bacteriophage $P_R$ promoter (PlambdaR*(−35), (Mermet-Bouvier & Chauvat, 1994, Current Microbiology, vol. 28, pp 145-148)).
- upper cases corresponding to the sequence of the repressor protein cI of the lambda bacteriophage where nucleotides 196-CTTGCG-201 were changed by 196-GCGACA-201 generating two amino-acid changes Leu66Ala and Ala67Thr (Mermet-Bouvier & Chauvat, 1994, Current Microbiology, vol. 28, pp 145-148). This sequence was called cI*3.
- bold upper cases homologous to TTadc transcriptional terminator sequence in reverse orientation (transcription terminator of the adc gene from *Clostridium acetobutylicum*, homologous from 179847 to 179807 of the pSLO1 megaplasmid).
- underlined upper cases corresponding to ApaI, PacI and SfiI To construct pMA-RQ-TTadc-CI*0-PlambdaR*(−35)-RBS01*2, the XmnI/NsiI fragment NsiI-CI*3-PlambdaR*(−35)-RBS01*2-XmnI purified from pMA-RQ-TTadc-CI*3-PlambdaR*(−35)-RBS01*2 described above was cloned between the XmnI and NsiI sites of plasmid pMA-RQ-TTadc-CI*1-PlambdaR*(−35)-RBS01*2 described above creating the wild type allele of the cI protein repressor. The resulting plasmid was verified by DNA sequencing and called pMA-RQ-TTadc-CI*0-PlambdaR*(−35)-RBS01*2.

Construction of Plasmid pUC18-TTadc-CI*0-PlambdaR*(−35)-ΔpgaABCD::TT02-TTadc-PlambdaR*(−35)-RBS01-thrA*1-cysE-PgapA-metA*11::Cm pUC18-TTadc-CI*0-PlambdaR*(−35)-ΔpgaABCD::TT02-TTadc-PlambdaR*(−35)-RBS01-thrA*1-cysE-PgapA-metA*11::Cm plasmid is derived from pUC18-ΔpgaABCD::TT02-TTadc-PlambdaR*(−35)-RBS01-thrA*1-cysE-PgapA-metA*11::Cm described in EP10306164.4 and U.S. 61/406,249 patent applications and pMA-RQ-TTadc-CI*0-PlambdaR*(−35)-RBS01*2 describe above.

To construct pUC18-TTadc-CI*0-PlambdaR*(−35)-ΔpgaABCD::TT02-TTadc-PlambdaR*(−35)-RBS01-thrA*1-cysE-PgapA-metA*11::Cm, the ApaII/PsiI fragment TTadc-CI*0-PlambdaR*(−35), treated by Large (Klenow) Fragment of *E. coli* DNA Polymerase I, and purified from pMA-RQ-TTadc-CI*0-PlambdaR*(−35)-RBS01*2 was cloned between the SfoI sites of plasmid pUC18-ΔpgaABCD::TT02-TTadc-PlambdaR*(−35)-RBS01-thrA*1-cysE-PgapA-metA*11::Cm. The resulting plasmid was verified by restriction and called pUC18-TTadc-CI*0-PlambdaR*(−35)-ΔpgaABCD::TT02-TTadc-PlambdaR*(−35)-RBS01-thrA*1-cysE-PgapA-metA*11::Cm.

Finally, to construct pUC18-TTadc-CI*0-PlambdaR*(−35)-ΔpgaABCD::TT02-TTadc-PlambdaR*(−35)-RBS01-thrA*1-cysE-PgapA-metA*11::Tc, the FRT-Tc-FRT resistance cassette was amplified by PCR with primers Ome 1836-HindIII-K7-FRT-Tc-F (SEQ ID No 34) and Ome 1837-SmaI-BstZ17I-K7-FRT-Tc-R (SEQ ID No 35) using pLOI2065 as template.

Ome1836-HindIII-K7-FRT-Tc-F
(SEQ ID No 34)
<u>GCCCAAGCTT</u>TGTAGGCTGGAGCTGCTTCGAAGTTCCTATACTTTCTAG

AGAATAGGAACTTCGGAATAGGAACCGGATCAATTCATCGCGCGTC with
- underlined upper cases corresponding to HindIII restriction sites and extrabases,
- bold upper case sequence corresponding to the FRT sequence of plasmid pKD4 (Datsenko, K. A. & Wanner, B. L., 2000, PNAS, 97: 6640-6645),
- upper case sequence homologous to sequence of the tetracycline resistance gene located on pLOI2065 (Underwood et al., Appl Environ Microbiol. 2002 December; 68(12): 6263-6272).

Ome1837-SmaI-BstZ17I-K7-FRT-Tc-R
(SEQ ID No 35)
<u>TCCCCCGGGGTATAC</u>CATATGAATATCCTCCTTAGTTCCTATTCCGAAG

TTCCTATTCTCTAGAAAGTATAGGAACTTCGAATTGTCGACAAGCTAGC

TTGC with
- underlined upper cases corresponding to SmaI and BstZ17I restriction sites and extrabases,
- bold upper case sequence corresponding to the FRT sequence of plasmid pKD4 (Datsenko, K. A. & Wanner, B. L., 2000, PNAS, 97: 6640-6645),
- upper case sequence homologous to sequence of the tetracycline resistance gene located on pLOI2065 (Underwood et al., Appl Environ Microbiol. 2002 December; 68(12): 6263-6272).

The FRT-Tc-FRT PCR product was digested by BstZ17I and HindIII and treated by Large (Klenow) Fragment of *E. coli* DNA Polymerase I. The resulting fragment was then cloned between the BstZ17I and PacI which has been treated by Large (Klenow) Fragment of *E. coli* DNA Polymerase I. The selected plasmid has the tc resistance cassette in the same orientation than the amp resistance cassette of pUC18 plasmid and was verified by DNA sequencing and called pUC18-TTadc-CI*0-PlambdaR*(-35)-ΔpgaABCD::TT02-TTadc-PlambdaR*(-35)-RBS01*2-thrA*1-cysE-PgapA-metA*11::Tc.

3.1.2. Construction of Plasmid pUC18-TTadc-CI*0-PlambdaR*(-35)-ΔyjbI::TT02-SMC

To construct the ΔyjbI::TT02-MCS fragment, overlapping PCR between the upstream region of yjbI (upyjbI), the TT02 transcriptional terminator, the multiple cloning site (MCS) and the downstream region of yjbI (downyjbI) was done.

First, the fragment upyjbI-TT02-MCS was amplified from E. coli MG1655 genomic DNA using primers Ome 1852-SfoI-KpnI-DyjbI amont-F (SEQ ID No 36) and Ome 1853-SMC-TT02-DyjbI amont-R (SEQ ID No 37) by PCR. Then, the TT02-MCS-downyjbI fragment was amplified from E. coli MG1655 genomic DNA using primers Ome 1854-TT02-SMC-DyjbI aval-F (SEQ ID No 38) and Ome 1855-SfoI-KpnI-DyjbI aval-R (SEQ ID No 39) by PCR. Primers Ome 1853-SMC-TT02-DyjbI amont-R (SEQ ID No 37) and Ome 1854-TT02-SMC-DyjbI aval-F (SEQ ID No 38) have been designed to overlap through a 36 nucleotides-long region. Finally, the upyjbI-TT02-MCS-downyjbI fragment was amplified by mixing the upyjbI-TT02-MCS and the TT02-MCS-downyjbI amplicons and using primers Ome 1852-SfoI-KpnI-DyjbI amont-F (SEQ ID No 36) and Ome 1855-SfoI-KpnI-DyjbI aval-R (SEQ ID No 39). The resulting fusion PCR product was digested by SfoI and cloned between the EcoRI sites of plasmid pUC18-TTadc-CI*0-PlambdaR*(-35)-ΔpgaABCD::TT02-TTadc-PlambdaR*(-35)-RBS01-thrA*1-cysE-PgapA-metA*11::Cm, described above, which has been treated by Large (Klenow) Fragment of E. coli DNA Polymerase I. The resulting plasmid was verified by DNA sequencing and called pUC18-TTadc-CI*0-PlambdaR*(-35)-ΔyjbI::TT02-MCS.

```
Ome 1852-SfoI-KpnI-DyjbI amont-F
                                           (SEQ ID No 36)
CGTAGGCGCCGGTACCGAGTGCAGATCGGCTGGAAGGCG
``` with
- underlined upper cases corresponding to SfoI and KpnI restriction sites and extrabases,
- upper case sequence homologous to sequence upstream of the yjbI gene (4247987-4248009, reference sequence available on the ECOGENE website)

```
Ome 1853-SMC-TT02- DyjbI amont-R
                                           (SEQ ID No 37)
GCTTGTATACAACAGATAAAACGAAAGGCCCAGTCTTTCGACTGAGCCT
TTCGTTTTATTTGATGCATTTCTGTAGAATTTTACACTTATAGTATCAT
TACTGATTGAGACTTCA
``` with
- underlined upper case sequence for the BstZ17I restriction site and the beginning of a multiple cloning site,
- upper case sequence corresponding to the transcriptional terminator T$_1$ of E. coli rrnB (Orosz A, Boros I and Venetianer P. Eur. J. Biochem. 1991 Nov. 1; 201(3): 653-9)
- bold upper case sequence homologous to sequence downstream of the yjbI gene (4248931-4248980, reference sequence available on the ECOGENE website).

```
Ome 1854-TT02-SMC- DyjbI aval-F
                                           (SEQ ID No 38)
AGACTGGGCCTTTCGTTTTATCTGTTGTATACAAGCTTTACCTAGGGCC
CTTAATTAAATAATGAATAAGGGTGTTTAAGTAAAGGAAAACATCACCG
TTCCTGGCAT
``` with
- upper case sequence corresponding to the transcriptional terminator T1 of E. coli rrnB (Orosz A, Boros I and Venetianer P. Eur. J. Biochem. 1991 Nov. 1; 201(3): 653-9)
- bold upper case sequence containing a multiple cloning site: BstZ17I, HindIII, AvrII, ApaI, PacI,
- underlined upper case sequence homologous to sequence downstream of the yjbI gene (4250286-4250335, reference sequence available on the ECOGENE website).

```
Ome 1855-SfoI-KpnI- DyjbI aval-R
                                           (SEQ ID No 39)
CGTAGGCGCCGGTACCCAGCATAATCATTCACCACACATCCG
``` with
- underlined upper cases corresponding to SfoI and KpnI restriction sites and extrabases,
- upper case sequence homologous to sequence upstream of the yjbI gene (4251224-4251249, reference sequence on the website http://ecogene.org/)

3.1.3. Construction of Plasmid pUC18-TTadc-CI*0-PlambdaR*(-35)-DyjbI::TT02-TTadc-PlambdaR*(-35)-RBS01-thrA*1-cysE-PgapA-metA*11::Tc To construct pUC18-TTadc-CI*0-PlambdaR*(-35)-DyjbI::TT02-TTadc-PlambdaR*(-35)-RBS01-thrA*1-cysE-PgapA-metA*11::Tc, the BstZ17I/SmaI fragment PlambdaR*(-35)-RBS01-thrA*1-cysE-PgapA-metA*11::Tc purified from pUC18-TTadc-CI*0-PlambdaR*(-35)-ΔpgaABCD::TT02-TTadc-PlambdaR*(-35)-RBS01-thrA*1-cysE-PgapA-metA*11::Tc was cloned between the PacI/BstZ17I sites of plasmid pUC18-TTadc-CI*0-PlambdaR*(-35)-ΔyjbI::TT02-SMC that had been treated by Large (Klenow) Fragment of E. coli DNA Polymerase I. The selected plasmid has the tc resistance cassette in the same orientation than the amp resistance cassette of pUC18 plasmid and was verified by DNA sequencing and called pUC18-TTadc-CI*0-PlambdaR*(-35)-DyjbI::TT02-TTadc-PlambdaR*(-35)-RBS01-thrA*1-cysE-PgapA-metA*11::Tc 3.2. Construction of Strain MG1655 metA*11 DyjbI::TT02-TTadc-PlambdaR*(-35)-RBS01-thrA*1-cysE-PgapA-metA*11::Tc pKD46

To replace the yjbI gene by the TT02-TTadc-PlambdaR*(-35)-RBS01-thrA*1-cysE-PgapA-metA*11::Tc region, pUC18-TTadc-CI*0-PlambdaR*(-35)-DyjbI::TT02-TTadc-PlambdaR*(-35)-RBS01-thrA*1-cysE-PgapA-metA*11::Tc was digested by AhdI and KpnI restriction enzymes and the remaining digested fragment ΔyjbI::TT02-TTadc-PlambdaR*(-35)-RBS01-thrA*1-cysE-PgapA-metA*11::Tc was introduced into strain MG1655 metA*11 pKD46 according to Protocol 1.

Tetracycline resistant recombinants were selected and the presence of the ΔyjbI::TT02-TTadc-PlambdaR*(-35)-RBS01-thrA*1-cysE-PgapA-metA*11::Tc chromosomal modification was verified by PCR with primers Ome1856-DyjbI-verif1-F (SEQ ID No 40), Ome1857-DyjbI-verif2-R (SEQ ID No 41), Ome 1838-K7-FRT-Tc-seq-F (SEQ ID No 42), and Ome1815-metA*11-seq-F (SEQ ID No 43) (Table 7) and by DNA sequencing. The verified and selected strain was called MG1655 metA*11 ΔyjbI::TT02-TTadc-PlambdaR*(−35)-RBS01-thrA*1-cysE-PgapA-metA*11::Tc (pKD46).

3.3. Transduction of ΔyjbI::TT02-TTadc-PlambdaR*(−35)-RBS01-thrA*1-cysE-PgapA-metA*11::Tc into Strain 4

The ΔyjbI::TT02-TTadc-PlambdaR*(−35)-RBS01-thrA*1-cysE-PgapA-metA*11::Tc chromosomal modification was transduced into strain 4 (Table 6), described above, with a P1 phage lysate from strain MG1655 metA*11 pKD46 ΔyjbI::TT02-TTadc-PlambdaR*(−35)-RBS01-thrA*1-cysE-PgapA-metA*11::Tc described above, according to Protocol 2. Tetracycline resistant transductants were selected and the presence of the ΔyjbI::TT02-TTadc-PlambdaR*(−35)-RBS01-thrA*1-cysE-PgapA-metA*11::Tc chromosomal modification was verified by PCR with Ome1856-DyjbI-verif1-F (SEQ ID No 40), Ome1857-DyjbI-verif2-R (SEQ ID No 41), Ome 1838-K7-FRT-Tc-seq-F (SEQ ID No 42), and Ome1815-metA*11-seq-F (SEQ ID No 43) (Table 2). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11::Cm DyjbI::TT02-TTadc-PlambdaR*(−35)-RBS01-thrA*1-cysE-PgapA-metA*11::Tc was called strain 5 (Table 6).

4. Construction of Strain 6: MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11::Cm ΔyjbI::TT02-TTadc-PlambdaR*(−35)-RBS01-thrA*1-cysE-PgapA-metA*11::Tc ΔmelB::TT02-TTadc-PlambdaR*(−35)-RBS01-thrA*1-cysE-PgapA-metA*11::Gt 4.1. Construction of Plasmid pUC18-TTadc-CI*0-PlambdaR*(−35)-ΔmelB::TT02-TTadc-PlambdaR*(−35)-RBS01-thrA*1-cysE-PgapA-metA*11::Gt Plasmid pUC18-TTadc-CI*0-PlambdaR*(−35)-ΔmelB::TT02-TTadc-PlambdaR*(−35)-RBS01-thrA*1-cysE-PgapA-metA*11::Gt is derived from pUC18-TTadc-CI*0-PlambdaR*(−35)-ΔCP4-6::TT02-TTadc-PlambdaR*(−35)-RBS01-thrA*1-cysE-PgapA-metA*11::Gt and pUC18-TTadc-CI*0-PlambdaR*(−35)-ΔmelB::TT02-MCS::Gt described below.

4.1.1. Construction of Plasmid pUC18-TTadc-CI*0-PlambdaR*(−35)-ΔCP4-6::TT02-TTadc-PlambdaR*(−35)-RBS01-thrA*1-cysE-PgapA-metA*11::Gt Plasmid pUC18-TTadc-CI*0-PlambdaR*(−35)-ΔCP4-6::TT02-TTadc-PlambdaR*(−35)-RBS01-thrA*1-cysE-PgapA-metA*11::Gt is derived from pUC18-TTadc-CI*0-PlambdaR*(−35)-ΔCP4-6::TT02-SMC::Gt and pUC18-TTadc-CI*0-PlambdaR*(−35)-ΔpgaABCD::TTadc-PlambdaR*(−35)-RBS01-thrA*1-cysE-PgapA-metA*11::Cm described above.

Construction of pMA-ΔCP4-6::TT02-MCS::Gt

To construct plasmid pMA-ΔCP4-6::TT02-MCS::Gt, the FRT-Gt-FRT resistance cassette was amplified by PCR with primers BstZ17I-FRT-Gt-F (SEQ ID No 44) and HindIII-FRT-Gt-R (SEQ ID No 45) using p34S-Gm as template.

```
BstZ17I-FRT-Gt-F
                                        (SEQ ID No 45)
TCCCCCGGGGTATACTGTAGGCTGGAGCTGCTTCGAAGTTCCTATACTT

TCTAGAGAATAGGAACTTCGGAATAGGAACTTCATTTAGATGGGTACCG

AGCTCGAATTG
``` with
underlined upper case sequence for SmaI and BstZ17I restriction sites and extrabases,
bold upper case sequence corresponding to the FRT sequence (Datsenko, K. A. & Wanner, B. L., 2000, PNAS, 97: 6640-6645)
upper case sequence homologous to sequence of the gentamycin gene located on p34S-Gm (Dennis et Zyltra, AEM July 1998, p 2710-2715).

```
HindIII-FRT-Gt-R
                                        (SEQ ID No 45)
CCCAAGCTTCATATGAATATCCTCCTTAGTTCCTATTCCGAAGTTCCTA

TTCTCTAGAAAGTATAGGAACTTCGGCGCGGATGGGTACCGAGCTCGAA

TTG
``` with
underlined upper case sequence for the HindIII restriction site and extrabases,
bold upper case sequence corresponding to the FRT sequence (Datsenko, K. A. & Wanner, B. L., 2000, PNAS, 97: 6640-6645)
upper case sequence homologous to the sequence of the gentamycin gene located on p34S-Gm (Dennis et Zyltra, AEM July 1998, p 2710-2715).

The FRT-Gt-FRT PCR product was digested by BstZ17I and HindIII and cloned between the BstZ17I and HindIII sites of pMA-ΔCP4-6::TT02-MCS described in EP10306164.4 and U.S. 61/406,249 patent applications. The resulting plasmid was verified by DNA sequencing and called pMA-ΔCP4-6::TT02-MCS-Gt.

Construction of pUC18-TTadc-CI*0-PlambdaR*(−35)-ΔCP4-6::TT02-SMC::Gt

To construct pUC18-TTadc-CI*0-PlambdaR*(−35)-ΔCP4-6::TT02-SMC::Gt, the StuI/BsrBI fragment ΔCP4-6::TT02-SMC::Gt purified from pMA-ΔCP4-6::TT02-MCS::Gt, described above, was cloned between the EcoRI sites of plasmid pUC18-TTadc-CI*0-PlambdaR*(−35)-ΔpgaABCD::TT02-TTadc-PlambdaR*(−35)-RBS01-thrA*1-cysE-PgapA-metA*11::Cm that has been treated by Large (Klenow) Fragment of E. coli DNA Polymerase I. The resulting plasmid was verified by sequencing and called pUC18-TTadc-CI*0-PlambdaR*(−35)-ΔCP4-6::TT02-SMC::Gt To construct the final plasmid pUC18-TTadc-CI*0-PlambdaR*(−35)-ΔCP4-6::TT02-TTadc-PlambdaR*(−35)-RBS01-thrA*1-cysE-PgapA-metA*11::Gt, the ApaI/BamHI fragment TT02-TTadc-PlambdaR*(−35)-RBS01-thrA*1-cysE-PgapA-metA*11 purified from pUC18-TTadc-CI*0-PlambdaR*(−35)-ΔpgaABCD::TT02-TTadc-PlambdaR*(−35)-RBS01-thrA*1-cysE-PgapA-metA*11::Cm, described above, was cloned between the ApaI/BamHI sites of plasmid pUC18-TTadc-CI*0-PlambdaR*(−35)-ΔCP4-6::TT02-SMC::Gt. The resulting plasmid was verified by sequencing and called pUC18-TTadc-CI*0-PlambdaR*(−35)-ΔCP4-6::
TT02-TTadc-PlambdaR*(−35)-RBS01-thrA*1-cysE-
PgapA-metA*11::Gt 4.1.2. Construction of Plasmid pUC18-TTadc-CI*0-
PlambdaR*(−35)-ΔmelB::TT02-SMC To construct the ΔmelB::TT02-MCS fragment, overlapping PCR between the upstream region of melB (upmelB), the TT02 transcriptional terminator, the multiple cloning site (MCS) and the downstream region of melB (downmelB) was done. First, the fragment upmelB-TT02-MCS was amplified from E. coli MG1655 genomic DNA using primers Ome 1841-SfoI-KpnI-DmelB amont-F (SEQ ID No 46) and Ome 1842-SMC-TT02-DmelB amont-R (SEQ ID No 47) by PCR. Then, the TT02-MCS-downmelB fragment was amplified from E. coli MG1655 genomic DNA using primers Ome 1843-TT02-SMC-DmelB aval-F (SEQ ID No 48) and Ome 1844-SfoI-KpnI-DmelB aval-R (SEQ ID No 49) by PCR. Primers Ome 1842-SMC-TT02-DmelB amont-R (SEQ ID No 47) and Ome 1843-TT02-SMC-DmelB aval-F (SEQ ID No 48) have been designed to overlap through a 36 nucleotides-long region. Finally, the upmelB-TT02-MCS-downmelB fragment was amplified by mixing the upmelB-TT02-MCS and the TT02-MCS-downmelB amplicons and using primers Ome 1841-SfoI-KpnI-DmelB amont-F (SEQ ID No 46) and Ome 1844-SfoI-KpnI-DmelB aval-R (SEQ ID No 49). The resulting fusion PCR product was digested by SfoI and cloned between the EcoRI sites of plasmid pUC18-TTadc-CI*0-PlambdaR*(−35)-ΔpgaABCD::TT02-TTadc-PlambdaR*(−35)-RBS01-thrA*1-cysE-PgapA-metA*11::Cm, described above, which has been treated by Large (Klenow) Fragment of E. coli DNA Polymerase I. The resulting plasmid was verified by DNA sequencing and called pUC18-TTadc-CI*0-PlambdaR*(−35)-ΔmelB::TT02-MCS.

Ome 1841-SfoI-KpnI-DmelB amont-F
(SEQ ID No 46)
<u>CGTAGGCGCCGGTACC</u>GACCTCAATATCGACCCAGCTACGC with
underlined upper cases corresponding to SfoI and KpnI restriction sites and extrabases,
upper case sequence homologous to sequence upstream of the melB gene (4340489-4340513, reference sequence available on the ECOGENE website)

Ome 1842 (SMC-TT02-DmelB amont-R)
(SEQ ID No 47)
GCTTGTATACAACAGATAAAACGAAAGGCCCAGTCTTTCGACTGAGCCT

TTCGTTTTATTTGATGCATTGAAATGCTCATAGGGTATCGGGTCGC with
underlined upper case sequence for the BstZ17I restriction site and the beginning of a multiple cloning site,
upper case sequence corresponding to the transcriptional terminator T1 of E. coli rrnB (Orosz A, Boros I and Venetianer P. Eur. J. Biochem. 1991 Nov. 1; 201(3): 653-9)
bold upper case sequence homologous to sequence downstream of the melB gene (4341377-4341406, reference sequence available on the ECOGENE website).

Ome 1843 (TT02-SMC-DmelB aval-F)
(SEQ ID No 48)
AGACTGGGCCTTTCGTTTTATCTGTTGTATACAAGCTTAATTAACCTAG

GGCCCGGGCGGATCC<u>GTGAGTGATGTGAAAGCCTGACGTGG</u> with
upper case sequence corresponding to the transcriptional terminator T1 of E. coli rrnB (Orosz A, Boros I and Venetianer P. Eur. J. Biochem. 1991 Nov. 1; 201(3): 653-9)
bold upper case sequence containing a multiple cloning site: BstZ17I, HindIII, AvrII, ApaI, BamHI,
underlined upper case sequence homologous to sequence downstream of the melB gene (4342793-4342818, reference sequence available on the ECOGENE website).

Ome 1844 (SfoI-KpnI-DmelB aval-R)
(SEQ ID No 49)
<u>CGTAGGCGCCGGTACC</u>CGAACTGCACTAAGTAACCTCTTCGG underlined upper cases corresponding to SfoI and KpnI restriction sites and extrabases,
upper case sequence homologous to sequence upstream of the melB gene (4343694-4343719, reference sequence available on the ECOGENE website)

4.1.3. Construction of Plasmid pUC18-TTadc-CI*0-PlambdaR*(−35)-ΔmelB::TT02-TTadc-PlambdaR*(−35)-RBS01-thrA*1-cysE-PgapA-metA*11::Gt To construct pUC18-TTadc-CI*0-PlambdaR*(−35)-ΔmelB::TT02-TTadc-PlambdaR*(−35)-RBS01-thrA*1-cysE-PgapA-metA*11::Gt, the BstZ17I/BamHI fragment PlambdaR*(−35)-RBS01-thrA*1-cysE-PgapA-metA*11::Gt purified from pUC18-TTadc-CI*0-PlambdaR*(−35)-ΔCP4-6::TT02-TTadc-PlambdaR*(−35)-RBS01-thrA*1-cysE-PgapA-metA*11::Gt, described above, was cloned between the BstZ17I/BamHI sites of plasmid pUC18-TTadc-CI*0-PlambdaR*(−35)-ΔmelB::TT02-SMC, described above. The resulting plasmid was verified by sequencing and called pUC18-TTadc-CI*0-PlambdaR*(−35)-DmelB::TT02-TTadc-PlambdaR*(−35)-RBS01-thrA*1-cysE-PgapA-metA*11::Gt.

4.2. Construction of Strain MG1655 metA*11 DmelB::TT02-TTadc-PlambdaR*(−35)-RBS01-thrA*1-cysE-PgapA-metA*11::Gt pKD46

To replace the melB gene by the TT02-TTadc-PlambdaR*(−35)-RBS01-thrA*1-cysE-PgapA-metA*11::Gt region, pUC18-TTadc-CI*0-PlambdaR*(−35)-ΔmelB::TT02-TTadc-PlambdaR*(−35)-RBS01-thrA*1-cysE-PgapA-metA*11::Gt was digested by AhdI and SphI restriction enzymes and the remaining digested fragment ΔmelB::TT02-TTadc-PlambdaR*(−35)-RBS01-thrA*1-cysE-PgapA-metA*11::Gt was introduced into strain MG1655 metA*11 pKD46 according to Protocol 1.

Gentamycin resistant recombinants were selected and the presence of the ΔmelB::TT02-TTadc-PlambdaR*(−35)-RBS01-thrA*1-cysE-PgapA-metA*11::Gt chromosomal modification was verified by PCR with primers Ome 1845-DmelB-verif1-F (SEQ ID No 50) and Ome 1846-DmelB-verif2-R (SEQ ID No 51) (Table 7), and by DNA sequencing. The verified and selected strain was called MG1655 metA*11 ΔmelB::TT02-TTadc-PlambdaR*(−35)-RBS01-thrA*1-cysE-PgapA-metA*11::Gt (pKD46).

4.3. Transduction of ΔmelB::TT02-TTadc-PlambdaR*(−35)-RBS01-thrA*1-cysE-PgapA-metA*11::Gt into strain 5

The ΔmelB::TT02-TTadc-PlambdaR*(−35)-RBS01-thrA*1-cysE-PgapA-metA*11::Gt chromosomal modification was transduced into strain 5 (Table 6), described above, with a P1 phage lysate from strain MG1655 metA*11 pKD46 ΔmelB::TT02-TTadc-PlambdaR*(−35)-RBS01-thrA*1-cysE-PgapA-metA*11::Gt described above, according to Protocol 2.

Gentamycin resistant transductants were selected and the presence of the ΔmelB::TT02-TTadc-PlambdaR*(−35)-RBS01-thrA*1-cysE-PgapA-metA*11::Gt chromosomal modification was verified by PCR with Ome 1845-DmelB-verif1-F (SEQ ID No 50) and Ome 1846-DmelB-verif2-R (SEQ ID No 51) (Table 7). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11::Cm ΔyjbI::TT02-TTadc-PlambdaR*(−35)-RBS01-thrA*1-cysE-PgapA-metA*11::Tc ΔmelB::TT02-TTadc-PlambdaR*(−35)-RBS01-thrA*1-cysE-PgapA-metA*11::Gt was called strain 6.

5. Construction of Strain 8: MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-PlambdaR*(−35)-thrA*1-cysE pBeloBAC11-PL1*1/RBS01*2-thrA*1-SMC-cysE-PgapA-metA*11-T7TΦ

5.1. Construction of Strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-PlambdaR*(−35)-thrA*1-cysE Promoter chromosomal modifications Ptrc-metH, PtrcF-cysPUWAM, PtrcF-cysJIH, Ptrc09-gcvTHP and Ptrc36-ARNmst17-metF, which have been described in WO2007/077041 and in WO2009/043803 patent applications, and ΔmetJ, ΔpykF, ΔpurU and ΔyncA genes deletions, which have been described in WO2007/077041, in WO2009/043803 and in WO2005/111202 patent applications, were transduced into a strain containing a metA*11 alleles which encodes an homoserine succinyltransferase with reduced feed-back sensitivity to S-adenosylmethionine and/or methionine as described in WO2005/111202, according to Protocol 2.

Resistance cassette, associated with each chromosomal modification or deletion during the construction of the strain have been removed according to Protocol 1.

The ΔmalS::TTadc-CI857-PlambdaR*(−35)-thrA*1-cysE::Km chromosomal modification was transduced into the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA with a P1 phage lysate from strain MG1655 metA*11 pKD46 ΔmalS::TTadc-CI857-PlambdaR*(−35)-thrA*1-cysE::Km described in EP10306164.4 and U.S. 61/406,249 patent applications, according to Protocol 2.

Kanamycin resistant transductants were selected and the presence of ΔmalS::TTadc-CI857-PlambdaR*(−35)-thrA*1-cysE::Km chromosomal modification was verified by PCR with primers Ome 0826-malS-F (SEQ ID No 52) and Ome 0827-malS-R (SEQ ID No 53) (Table 7). The resulting strain has the genotype MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-PlambdaR*(−35)-thrA*1-cysE::Km Finally, the kanamycin resistance of the above strain was removed according to Protocol 1. The loss of the kanamycin resistant cassette was verified by PCR by using the primers Ome 0826-malS-F (SEQ ID No 52) and Ome 0827-malS-R (SEQ ID No 53). The resulting strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-PlambdaR*(−35)-thrA*1-cysE was called strain 7.

5.1.1. Construction of Strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-PlambdaR*(−35)-thrA*1-cysE pBeloBAC11-PL1*1/RBS01*2-thrA*1-SMC-cysE-PgapA-metA*11-T7TΦ

Construction of pBeloBAC11-PL1*1/RBS01*2-thrA*1-SMC-cysE-PgapA-metA*11-T7TΦ Plasmid Plasmid pBeloBAC11-PL1*1/RBS01*2-thrA*1-SMC-cysE-PgapA-metA*11-T7TΦ plasmid is derived from plasmid pBeloBAC11-PT7/RBST7-thrA*1-SMC-cysE-PgapA-metA*11-T7TΦ described in example 2 of this patent application.

To construct plasmid pBeloBAC11-PL1*1/RBS01*2-thrA*1-SMC-cysE-PgapA-metA*11-T7TΦ, plasmid pBeloBAC11-PT7/RBST7-thrA*1-SMC-cysE-PgapA-metA*11-T7TΦ was amplified with primers Ome 2012-SfoI-HpaI-AvrII-PL1*1/RBS01*2-thrA*1-F (SEQ ID No 54) and Ome 0625-Ptrc-cysE*rec (SEQ ID No 55). The HpaI/NheI digested PL1*1/RBS01*2-thrA*1 fragment was cloned between the HpaI and NheI sites of the plasmid pBeloBAC11-PT7/RBST7-thrA*1-SMC-cysE-PgapA-metA*11-T7TΦ described in example 2 of this patent application. The resulting plasmid was verified by DNA sequencing and called pBeloBAC11-PL1*1/RBS01*2-thrA*1-SMC-cysE-PgapA-metA*1'-T7TΦ.

Ome 2012 SfoI-HpaI-AvrII-PL1*1/RBS01*2-thrA*1-F
(SEQ ID No 54)
<u>TGCCGGCACGGCGCCAAGTTAACCCTAGG</u>TTATCTCTGGCGGTGTTGAC

ATAAATACCACTGGCGGTTATACTGAGCACAtcaac*TAAGGAGGTATA*

*AATGAGAGTGTTGAAGTTCG* with
- underlined upper cases corresponding to SfoI, HpaI and AvrII restriction sites and extrabases,
- bold upper case sequence corresponding to short form of lambda bacteriophage $P_L$ promoter ($P_{L1}$ Giladi et al, FEMS Microbiol Rev. 1995 August; 17(1-2):135-40) and harbouring a mutation in −10 boxes (G-12T described in Kincade & deHaseth, Gene. 1991 Jan. 2; 97(1):7-12). This promoter is called PL1*1).
- lower cases: five bases spacing the transcriptional start site of PL1*1 and the ribosome binding site RBS01*2
- italic upper cases corresponding to RBS01*2 sequence
- underlined upper case sequence homologous to thrA*1 gene (337-354, reference sequence available on the ECOGENE website).

Ome 0625 Ptrc-cysE*rec
(SEQ ID No 55)
CCGGGTCAGCGGCGTAGGC homologous to cysE gene (3780360-3780378, reference sequence available on the ECOGENE website)

The pBeloBAC11-PL1*1/RBS01*2-thrA*1-SMC-cysE-PgapA-metA*11-T7TΦ, described above, was introduced by electroporation into strain 7 (Table 6). The presence of plasmid pBeloBAC11-PL1*1/RBS01*2-thrA*1-SMC-cysE-PgapA-metA*11-T7TΦ was verified and the resulting strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpurU ΔyncA ΔmalS::TTadc-CI857-Plamb-daR*(−35)-thrA*1-cysE pBeloBAC11-PL1*1/RBS01*2-thrA*1-SMC-cysE-PgapA-metA*11-TT01 was called strain 8.

TABLE 7

Primers used for PCR verifications of chromosomal modifications described above

| Genes name | Primers name | SEQ ID No | Location of the homology with the chromosomal region | Sequences |
|---|---|---|---|---|
| wcaM | Ome1707-DwcaM_verif_F | 30 | 2115741-2115762 | GCCGTTCAACACTGGCTGGACG |
|  | Ome1708-DwcaM_verif_R | 31 | 2110888-2110907 | TGCCATTGCAGGTGCATCGC |
| yjbI | Ome1856-DyjbI-verif1-F | 40 | 4247754-4247774 | CAGACCACCCAACTGGCGACC |
|  | Ome1857-DyjbI -verif2-R | 41 | 4251489-4251508 | GCCATTGGAATCGACCAGCC |
|  | Ome 1838-K7-FRT-Tc-seq-F | 42 |  | GGTTGCTGGCGCCTATATCGC |
|  | Ome 1815-metA*11-seq-F | 43 | 4212634-4212658 | GCCTGGTGGAGTTTAATGATGTCGC |
| melB | Ome 1845-DmelB-verif1-F | 50 | 4340168-4340187 | GCCGATTTTGTCGTGGTGGC |
|  | Ome 1846-DmelB-verif2-R | 51 | 4344044-4344065 | GCCGGTTATCCATCAGGTTCAC |
| malS | Ome0826-malS-F | 52 | 3734778-3734800 | GGTATTCCACGGGATTTTTCGCG |
|  | Ome0827-malS-R | 53 | 3738298-3738322 | CGTCAGTAATCACATTGCCTGTTGG |

Example IV: Evaluation of Temperature Dependent Methionine Production of Strains 3, 4, 5 and 6

Production strains were evaluated in small Erlenmeyer flasks. A 5.5 mL preculture was grown for 21 hours in a mixed medium (10% LB medium (Sigma 25%) with 2.5 g·L$^{-1}$ glucose and 90% minimal medium PC1). It was used to inoculate a 50 mL culture to an OD$_{600}$ of 0.2 in medium PC1. When it was necessary, gentamycin was added at a concentration of 10 mg·L$^{-1}$, chloramphenicol at 30 mg·L$^{-1}$ and tetracycline at 5 mg·L$^{-1}$. When the culture had reached an OD$_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation.

The culture and preculture conditions are shown in tables below. Precultures were grown either at 30° C. or 37° C. Cultures were grown either at 30° C. or 37° C. or at 37° C. for 2 hours, then at 42° C. for 2 hours and finally 37° C. for the rest of the culture.

TABLE 8

Minimal medium composition (PC1).

| Compound | Concentration (g · L$^{-1}$) |
|---|---|
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |
| Citric acid | 6.00 |
| CaCl$_2$•2H$_2$O | 0.04 |
| K$_2$HPO$_4$ | 8.00 |
| Na$_2$HPO$_4$ | 2.00 |
| (NH$_4$)$_2$HPO$_4$ | 8.00 |
| NH$_4$Cl | 0.13 |
| NaOH 4M | Adjusted to pH 6.8 |
| FeSO$_4$•7H$_2$O | 0.04 |
| Thiamine | 0.01 |
| Glucose | 15.00 |
| Ammonium thiosulfate | 5.60 |
| Vitamin B12 | 0.01 |
| MOPS | 15.00 |

TABLE 9

Methionine yield ($Y_{met}$) in % g methionine/g de glucose produced in batch culture by the strain 3. For the precise definition of methionine/glucose yield see below.

| Growth conditions of precultures and cultures of strain 3 | $Y_{met}$ | SD |
|---|---|---|
| Strain 3 - PC 30° C./C 30° C. (n = 4) | 7.9 | 0.5 |
| Strain 3 - PC 30° C./C 37° C. (n = 34) | 9.0 | 1.0 |
| Strain 3 - PC 30° C./C 37-42-37° C. (n = 86) | 9.2 | 1.2 |
| Strain 3 - PC 37° C./C37° C. (n = 3) | 7.9 | 0.1 |

SD denotes the standard deviation for the yields that was calculated on the basis of several repetitions (n = number of repetitions). Different culture conditions were tested. They are indicated in the table;
PC means preculture and C means culture.

As shown in table 9 thermo-induction of the expression of genes thrA*1 and cysE during the culture process increases the amount of methionine produced. Constitutive expression throughout the culture process results in low methionine yield.

For an optimal methionine production, the best culture conditions are 30° C. for the preculture followed by a culture at 37° C. (2 h), 42° C. (2 h), 37° C. In such conditions, strain 3 produced methionine with a yield of 9.2%.

TABLE 10

Methionine yield ($Y_{met}$) in % g methionine/g de glucose produced in batch culture by strains 4, 5 and 6. For the precise definition of methionine/glucose yield see below.

| Strain and growth condition | Ymet | SD |
|---|---|---|
| Strain 4 - PC 30° C./C 37-42-37° C. (n = 11) | 9.7 | 1.7 |
| Strain 5 - PC 30° C./C 37-42-37° C. (n = 9) | 10.6 | 1.3 |
| Strain 6 - PC 30° C./C 37-42-37° C. (n = 3) | 11.7 | 0.1 |

SD denotes the standard deviation for the yields that was calculated on the basis of several repetitions (n = number of repetitions). Precultures were cultivated at 30° C. and culture at 37° C. for 2 hours, 42° C. for 2 hours and 37° C. until the culture end.

Strains 4, 5 and 6 were all cultivated in conditions for optimal methionine production.

As shown in table 10, thermo-induction of the expression of genes thrA*1 and cysE during the culture process increases the production proportionally to the copy number of the genes controlled by the inducible promoter. Indeed, strain 6 possessing seven copies of thrA*1 under the control of Plambda promoter (see table 6) produced methionine with a higher yield than strains 5 (6 copies of thr*1) and 4 (5 copies).

It is noteworthy to precise that strains 5 and 6 cannot grow at a constant temperature of 37° C. In conclusion these results demonstrate that thermo-induction is not only better for the production but also essential in such case.

Extracellular methionine concentration was quantified by HPLC after OPA/FMOC derivatization. The residual glucose concentration was analyzed using HPLC with refractometric detection. The methionine yield was expressed as followed:

$$Y_{met} = \frac{\text{methionine}(g)}{\text{consummed glucose}(g)} * 100$$

To validate the thermo-induction of the expression of thrA*1 and cysE genes, the activities of the corresponding enzymes were determined in crude extracts.

For the determination of enzyme activities in vitro, *E. coli* strains were cultured in minimal medium as described above and harvested at the end of the exponential growth phase by centrifugation. Pellets were resuspended in cold 20 mM potassium phosphate buffer (pH 7.2) containing a tablet of protease inhibitor cocktail with EDTA. Then, cells were lysed 1×30 s at 6500 rpm by bead beating with a Precellys system (Bertin Technologies) followed by centrifugation at 12000 g (4° C.) for 30 minutes. Supernatants were desalted and used for analysis. Protein concentrations were determined using Bradford assay reagent (Bradford, 1976).

For the determination of HDH activity (Homoserine Dehydrogenase, encoded by thrA*1) in vitro, 15 µg of cell crude extract were assayed in 100 mM Tris-HCl pH9, 150 mM KCl, 1 mM NADP+ and 25 mM L-Homoserine. NADP+ reduction in presence of L-homoserine was monitored spectrophotometrically for 30 minutes at 340 nm.

SAT activity (Serine Acetyl Transferase, encoded by cysE) was assayed spectrophotometrically at 25° C. by measuring the absorbance of TNB at 408 nm for 10 minutes, due to the reaction of CoA with DTNB. Reaction was done with 2 µg of crude extracts in 80 mM potassium phosphate pH7.5, 2 mM acetyl-coA, 30 mM serine and 0.1 mM DTNB.

TABLE 11

Homoserine dehydrogenase (HDH, thrA*1) and serine acetyltransferase (SAT, cysE) activities were determined on the crude extracts of cultures of strain 3 grown in different conditions. Activities are given in mUI/mg of proteins.

| Growth conditions of precultures and cultures of strain 3 | HDH | SAT | N |
|---|---|---|---|
| Preculture 30° C. + Culture 30° C. | 78 ± 28 | 99 ± 10 | 6 |
| Preculture 30° C. + Culture 37° C. | 104 ± 21 | 153 ± 28 | 18 |
| Preculture 30° C. + Culture 37/42/37° C. | 195 ± 33 | 324 ± 32 | 16 |
| Preculture 37° C. + Culture 37° C. | 94 ± 25 | 181 ± 20 | 6 |

Standard deviations were calculated on the basis of several independent cultures (N = number of repetitions).

Table 11 shows that upon induction HDH and SAT activities are increased. Constitutive expression of thrA*1 and cysE results in levels of HDH and SAT activities that are between non-induced and induced conditions, explaining in part the lower methionine yield. In conclusion these results demonstrate that the induction of thrA*1 and cysE is truly beneficial for increasing methionine yield.

In the same manner for strains 4, 5 and 6, HDH and SAT activities increased upon induction. Activities increase proportionally with the copy-number of the genes thrA*1 and cysE integrated on the chromosome (Data not shown).

Example V: Evaluation of Temperature Dependent Methionine Production of Strain 8

Strain 8 was evaluated in small Erlenmeyer flasks as described in example IV. It was compared to strain 3.

TABLE 12

Methionine yield ($Y_{met}$) in % g methionine/g de glucose produced in batch culture by strains 8 and 3. For the precise definition of methionine/glucose yield see below.

| Growth conditions of strains 3 and 8 | Ymet | SD |
|---|---|---|
| Strain 8 - PC 30° C./C 37-42-37° C. (n = 3) | 9.5 | 0.1 |

TABLE 12-continued

Methionine yield ($Y_{met}$) in % g methionine/g de glucose produced in batch culture by strains 8 and 3. For the precise definition of methionine/glucose yield see below.

| Growth conditions of strains 3 and 8 | Ymet | SD |
|---|---|---|
| Strain 3 - PC 30° C./C 37-42-37° C. (n = 3) | 8.6 | 0.5 |

SD denotes the standard deviation for the yields that was calculated on the basis of several repetitions (n = number of repetitions). Precultures were cultivated at 30° C. and culture at 37° C. for 2 hours, 42° C. for 2 hours and then 37° C. until the end of the culture.

As shown in table 12, methionine production upon induction is as good for strain 8 carrying construction PL1*1/RBS01*2-thrA*1-SMC-cysE as for strain 3 carrying 4 copies of construction PlambdaR*(−35)-RBS01-thrA*1-cysE.

Extracellular methionine concentration was quantified by HPLC after OPA/FMOC derivatization. The residual glucose concentration was analyzed using HPLC with refractometric detection. The methionine yield was expressed as followed:

$$Y_{met} = \frac{\text{methionine}(g)}{\text{consummed glucose}(g)} * 100$$

To validate the thermo-induction of the expression of thrA*1 and cysE genes controlled by the PL1*1 inducible promoter, the activities of the corresponding enzymes were determined in crude extracts as described in example IV.

TABLE 13

Homoserine dehydrogenase (HDH, thrA*1) and serine acetyltransferase (SAT, cysE) activities were determined in the above described cultures and were given in mUI/mg of proteins.

| Growth conditions of strain 3 and 8 | HDH | SAT | N |
|---|---|---|---|
| Strain 8 - Preculture 30° C. + Culture 37/42/37° C. | 91 ± 8 | 140 ± 2 | 3 |
| Strain 3 - Preculture 30° C. + Culture 37/42/37° C. | 100 ± 3 | 140 ± 10 | 2 |

Standard deviations were calculated on the basis of several independent cultures (N = number of repetitions).

As can be seen in table 13, the HDH and SAT activities of strain 8 were similar to that of strain 3. As a result, induction from PL1*1/RBS01*2-thrA*1-SMC-cysE is at least equivalent to induction from 4 copies of PlambdaR* (−35)-RBS01-thrA*1-cysE.

REFERENCES

Saunderson, C. L., (1985) British Journal of Nutrition 54, 621-633.

"Microbial conversion of glycerol to 1,3-propanediol by an engineered strain of Escherichia coli." Tang X, Tan Y, Zhu H, Zhao K, Shen W. Appl Environ Microbiol. 2009 March; 75(6):1628-34.

"A genetic switch". Ptashne M. Blackwell Scientific, Cambridge, Mass. 1986.

"A genetic switch: Phage lambda revisited". Ptashne M. Cold Spring Harbor Lab Press. Cold Spring Harbor, N.Y. 2004.

"The bacteriophages, Part II: Life of phages, 8". Gene regulatory circuitry of phage λ. Little J. $2^{nd}$ edition 2004. Richard Calendar. ed. Oxford University Press.

"On a thermosensitive repression system in the Escherichia coli lambda bacteriophage". Sussman R, Jacob F. C. R. Hebd. Seances Acad. Sci. 1962, 254, p 1517.

The invention claimed is:

1. A method for the production of methionine or its derivatives in a fermentative process comprising:

culturing a modified microorganism from *Escherichia coli* in an appropriate culture medium comprising a source of carbon, a source of sulphur and a source of nitrogen, to produce methionine or its derivatives, wherein in said modified microorganism, expression of five, six, or seven copies of homoserine dehydrogenase (thrA) and serine acetyltransferase (cysE) genes involved in methionine production are under direct control of a heterologous temperature-inducible promoter, inducing expression of the homoserine dehydrogenase (thrA) and serine acetyltransferase (cysE) genes through thermo-induction by up-shifting the temperature, and recovering methionine and/or a derivative thereof from said culture medium.

2. The method of claim 1, wherein said temperature-inducible promoter is selected from the group consisting of promoters regulated by a modified repressor of phage lambda, the promoter PR or a derivative of PR, the promoter PL or a derivative of PL and a modified lac promoter regulated by a temperature sensitive Lac repressor.

3. The method of claim 2, wherein said modified repressor of phage lambda is the lambda repressor allele cI857 or any other temperature labile allele of the lambda repressor cI.

4. The method of claim 2, wherein in the modified microorganism, the gene recA is deleted.

5. The method of claim 1, wherein said expression of thrA and cysE genes involved in methionine production is under indirect control of said heterologous temperature-inducible promoter, said genes being transcribed by a heterologous RNA polymerase, having an expression that is under control of an inducible promoter.

6. The method of claim 5, wherein said heterologous RNA polymerase is selected from the group consisting of T7 and T3 polymerase.

7. The method of claim 1, wherein said microorganism further comprises at least one gene whose expression is under control, direct or indirect, of a heterologous inducible promoter selected from the group consisting of cysteine synthase (cysK), ORF upstream of cysK (cysZ), ATP sulfurylase (cysN), sulfate adenylyltransferase (cysD), adenylylsulfate kinase (cysC), Periplasmic sulfate-binding protein (sbp), phosphoenolpyruvate carboxylase (ppc), phosphoenolpyruvate synthase (pps), pyruvate carboxylase (pyc), acetyl-CoA synthetase (acs), homoserine O-transsuccinylase (metA), cystathionine gamma-synthase (metB), cystathionine beta-lyase (metC), 5-methyltetrahydropteroyltriglutamate-homocysteine S-methyltransferase (metE), 5,10-methylenetetrahydrofolate reductase (metF), B12-dependent homocysteine-N5-methyltetrahydrofolate transmethylase (met methionine adenosyltransferase (metK), aspartokinase II/homoserine dehydrogenase II (metL), aspartate-semialdehyde dehydrogenase (asd), aspartate aminotransferase (aspC), aspartokinase III (lysC), pyruvate kinase I (pykA), pyruvate kinase II (pykF) formyltetrahydrofolate deformylase (purU), the operons cysPUWAM (periplasmic sulphate binding protein, a component of sulphate ABC transporter, a membrane bound sulphate transport protein, a sulphate permease and an O-acetyl serine sulfhydralase), cysJIH (alpha and beta subunits of a sulfite reductase and an adenylylsulfate reductase) and gcvTHP (Tetrahydrofolate dependent aminomethyl transferase, a glycine cleavage, carrier of aminomethyl group and a glycine dehydrogenase), phosphoglycerate dehydrogenase (serA), phosphoserine phosphatase (serB), phosphoserine aminotransferase (serC), serine hydroxymethyl transferase (glyA), acetate kinase (ackA), phosphotransacetylase (pta), pyruvate dehydrogenase E1 (ace), pyruvate dehydrogenase E2 (aceF), lipoamide dehydrogenase (lpd), succinyl-CoA synthetase beta subunit (sucC), succinyl-CoA synthetase alpha subunit (sucD), phosphoenolpyruvate carboxykinase (pck), malate dehydrogenase (maeB), pyruvate oxidase (poxB), acetohydroxy acid synthase I large subunit (ilvB), acetohydroxy acid synthase I small subunit (ilvN), acetohydroxy acid synthase II large subunit (ilvG), acetohydroxy acid synthase II small subunit (ilvM), acetohydroxy acid synthase III large subunit (ilvI), acetohydroxy acid synthase III small subunit (ilvH), DAHP synthetase (aroF), DAHP synthetase (aroG), DAHP synthetase (aroH), homoserine kinase (thrB), threonine synthase (thrC), serine deaminase (sdaA), serine deaminase (sdaB), S-Adenosylmethionine decarboxylase (speD), ornithine decarboxylase (speC), arginine succinyltransferase (astA), dihydrodipicolinate synthase (dapA), malate dehydrogenase (mdh), malate dehydrogenase FAD/NAD(P)-binding domain (mqo), citrate synthase (gltA).

8. The method of claim 1, wherein the gene thrA is a thrA allele having reduced feedback sensitivity to threonine.

9. The method of claim 7, wherein the gene metA is a metA allele encoding enzyme with reduced feedback sensitivity to methionine and S-adenosylmethionine.

* * * * *

SEQUENCE LISTING

```
<160> NUMBER OF SEQ ID NOS: 55

<210> SEQ ID NO 1
<211> LENGTH: 117
<212> TYPE: DNA
<213> ORGANISM: Artificial Sequence
<220> FEATURE:
<223> OTHER INFORMATION: Ptrc07-serBF oligonucleotide

<400> SEQUENCE: 1
ccaccctttg aaaatttgag acttaatgtt gccagaagca atggatacaa ggtagcctca    60
tgctcacact ggctcacctt cgggtgggcc tttctgccat atgaatatcc tccttag     117

<210> SEQ ID NO 2
<211> LENGTH: 123
<212> TYPE: DNA
<213> ORGANISM: Artificial Sequence
<220> FEATURE:
<223> OTHER INFORMATION: Ptrc07-serBR oligonucleotide

<400> SEQUENCE: 2
cgcaccaggt aatgttaggc attaaggctc ctgtaaaatc gttcgaagca gggaaaataa    60
cttccacaca ttatacgagc cggatgatta atcgccaaca gcttgtaggc tggagctgct   120
tcg                                                                 123
```

```
<210> SEQ ID NO 3
<211> LENGTH: 19
<212> TYPE: DNA
<213> ORGANISM: Artificial Sequence
<220> FEATURE:
<223> OTHER INFORMATION: serBF oligonucleotide

<400> SEQUENCE: 3
caaggcaaga cagaacagg                                                   19

<210> SEQ ID NO 4
<211> LENGTH: 19
<212> TYPE: DNA
<213> ORGANISM: Artificial Sequence
<220> FEATURE:
<223> OTHER INFORMATION: serBR oligonucleotide

<400> SEQUENCE: 4
ggcatcactt catcaccac                                                   19

<210> SEQ ID NO 5
<211> LENGTH: 82
<212> TYPE: DNA
<213> ORGANISM: Artificial Sequence
<220> FEATURE:
<223> OTHER INFORMATION: ApaI-TTadc-CI857-F-1 oligonucleotide

<400> SEQUENCE: 5
accttgccga gggccctaaa ataagagtt accttaaatg gtaactctta ttttttttat       60
cagccaaacg tctcttcagg cc                                               82

<210> SEQ ID NO 6
<211> LENGTH: 95
<212> TYPE: DNA
<213> ORGANISM: Artificial Sequence
<220> FEATURE:
<223> OTHER INFORMATION: PlambdaR-thrA-R-2 oligonucleotide

<400> SEQUENCE: 6
caacactctc atatgacctc cttagtacat gcaaccatta tcaccgccag aggtaaaatt      60
gtcaacacgc acggtgttag atatttatcc cttgc                                 95

<210> SEQ ID NO 7
<211> LENGTH: 61
<212> TYPE: DNA
<213> ORGANISM: Artificial Sequence
<220> FEATURE:
<223> OTHER INFORMATION: PlambdaR-thrA-F-3 oligonucleotide

<400> SEQUENCE: 7
gcatgtacta aggaggtcat atgagagtgt tgaagttcgg cggtacatca gtggcaaatg      60
c                                                                      61

<210> SEQ ID NO 8
<211> LENGTH: 21
<212> TYPE: DNA
<213> ORGANISM: Artificial Sequence
<220> FEATURE:
<223> OTHER INFORMATION: cysE-R-4 oligonucleotide

<400> SEQUENCE: 8
agcttgcatg cctgcaggtc g                                                21

<210> SEQ ID NO 9
```

```
<211> LENGTH: 33
<212> TYPE: DNA
<213> ORGANISM: Artificial Sequence
<220> FEATURE:
<223> OTHER INFORMATION: SmaI-PgapA-F oligonucleotide

<400> SEQUENCE: 9
acgtcccggg caagcccaaa ggaagagtga ggc                                33

<210> SEQ ID NO 10
<211> LENGTH: 67
<212> TYPE: DNA
<213> ORGANISM: Artificial Sequence
<220> FEATURE:
<223> OTHER INFORMATION: PgapA-metA*11-R oligonucleotide

<400> SEQUENCE: 10
ggcgggtagc tcgtccggca cacgaatcgg catatattcc accagctatt tgttagtgaa    60
taaaagg                                                              67

<210> SEQ ID NO 11
<211> LENGTH: 67
<212> TYPE: DNA
<213> ORGANISM: Artificial Sequence
<220> FEATURE:
<223> OTHER INFORMATION: PgapA-metA*11-F oligonucleotide

<400> SEQUENCE: 11 cctttattc actaacaaat agctggtgga atatatgccg attcgtgtgc cggacgagct     60
acccgcc                                                              67

<210> SEQ ID NO 12
<211> LENGTH: 47
<212> TYPE: DNA
<213> ORGANISM: Artificial Sequence
<220> FEATURE:
<223> OTHER INFORMATION: BamHI-metA*11-R oligonucleotide

<400> SEQUENCE: 12
acgtggatcc gaattccgac tatcacagaa gattaatcca gcgttgg                  47

<210> SEQ ID NO 13
<211> LENGTH: 78
<212> TYPE: DNA
<213> ORGANISM: Artificial Sequence
<220> FEATURE:
<223> OTHER INFORMATION: SnaBI-thrA-SMC-cysE-F oligonucleotide

<400> SEQUENCE: 13
tgctacgtac cctctcatgg aagttaggag tctgagctag ctagtccgct cgagatacga    60
aagaagtccg cgaactgg                                                  78

<210> SEQ ID NO 14
<211> LENGTH: 18
<212> TYPE: DNA
<213> ORGANISM: Artificial Sequence
<220> FEATURE:
<223> OTHER INFORMATION: cysE-R oligonucleotide

<400> SEQUENCE: 14
caaccagtga ccgatgcg                                                  18

<210> SEQ ID NO 15
<211> LENGTH: 139
```

```
<212> TYPE: DNA
<213> ORGANISM: Artificial Sequence
<220> FEATURE:
<223> OTHER INFORMATION: SfoI-PT7-RBST7-NdeI-thrA-F  oligonucleotide

<400> SEQUENCE: 15
ggcgcctcga ttcgaacttc tgatagactt cgaaattaat acgactcact atagggagac      60
cacaacggtt ccctctaga aataattttg tttaactta agaaggagat atacatatga       120
gagtgttgaa gttcggcgg                                                  139

<210> SEQ ID NO 16
<211> LENGTH: 139
<212> TYPE: DNA
<213> ORGANISM: Artificial Sequence
<220> FEATURE:
<223> OTHER INFORMATION: metA-T7T?-SfoI-R oligonucleotide

<400> SEQUENCE: 16
ggcgcccttt cagcaaaaaa cccctcaaga cccgtttaga ggccccaagg ggttatgcta      60
gttattgctc agcggtggca gcagccaact cagcttcctt tcgggctttg ttagttaatc    120
cagcgttgga ttcatgtgc                                                  139

<210> SEQ ID NO 17
<211> LENGTH: 34
<212> TYPE: DNA
<213> ORGANISM: Artificial Sequence
<220> FEATURE:
<223> OTHER INFORMATION: HindIII-upmalS-F-1 oligonucleotide

<400> SEQUENCE: 17
atcgtaaagc ttttcacttt acctggcgca ttgg                                  34

<210> SEQ ID NO 18
<211> LENGTH: 45
<212> TYPE: DNA
<213> ORGANISM: Artificial Sequence
<220> FEATURE:
<223> OTHER INFORMATION: upmalS-Km-R-2 oligonucleotide

<400> SEQUENCE: 18
ctaaggagga tattcatatg accggttcgg cggcgttctg gatgg                      45

<210> SEQ ID NO 19
<211> LENGTH: 45
<212> TYPE: DNA
<213> ORGANISM: Artificial Sequence
<220> FEATURE:
<223> OTHER INFORMATION: upmalS-Km-F-3 oligonucleotide

<400> SEQUENCE: 19
ccatccagaa cgccgccgaa ccggtcatat gaatatcctc cttag                      45

<210> SEQ ID NO 20
<211> LENGTH: 65
<212> TYPE: DNA
<213> ORGANISM: Artificial Sequence
<220> FEATURE:
<223> OTHER INFORMATION: Km-SMC-R-4 oligonucleotide

<400> SEQUENCE: 20
gatcgatgga tccatctcga gatccgcgga tgtatacatg ggccctgtag gctggagctg      60
cttcg                                                                  65
```

<210> SEQ ID NO 21
<211> LENGTH: 36
<212> TYPE: DNA
<213> ORGANISM: Artificial Sequence
<220> FEATURE:
<223> OTHER INFORMATION: downmalS-F-1 oligonucleotide

<400> SEQUENCE: 21
atgctgaatt caccggtgaa gcctggggcc acggcg                                36

<210> SEQ ID NO 22
<211> LENGTH: 39
<212> TYPE: DNA
<213> ORGANISM: Artificial Sequence
<220> FEATURE:
<223> OTHER INFORMATION: downmalS-R-2 oligonucleotide

<400> SEQUENCE: 22
tacgatgaat cgggacgcc ataagcgtta tcaatcacc                              39

<210> SEQ ID NO 23
<211> LENGTH: 925
<212> TYPE: DNA
<213> ORGANISM: Artificial Sequence
<220> FEATURE:
<223> OTHER INFORMATION: Plasmid TTadc-CI857*-PlambdaR*(-35)-RBS01-SMC-
      TT07

<400> SEQUENCE: 23
gggccctaaa aataagagtt accttaaatg gtaactctta tttttttttat taattaacct     60
aggtcagcca acgtctctt caggccactg actagcgata actttcccca caacggaaca    120
actctcattg catgggatca ttgggtactg tgggtttagt ggttgtaaaa acacctgacc    180
gctatccctg atcagtttct tgaaggtaaa ctcatcaccc ccaagtctgg ctatgcagaa    240
atcacctggc tcaacagcct gctcagggtc aacgagaatt aacattccgt caggaaagct    300
tggcttggag cctgttggtg cggtcatgga attaccttca acctcaagcc agaatgcaga    360
atcactggct tttttggttg tgcttaccca tctctccgca tcacctttgg taaaggttct    420
aagcttaggt gagaacatcc ctgcctgaac atgagaaaaa acagggtact catactcact    480
tctaagtgac ggctgcatgc taaccgcttc atacatctcg tagatttctc tggcgattga    540
agggctaaat tcttcaacgc taactttgag aattttgta agcaatgcgg cgttgtaagc     600
atttaatgca ttgatgccat taaataaagc accaacgcct gactgcccca tccccatctt    660
gtctgcgaca gattcctggg ataagccaag ttcattttc ttttttttcat aaattgcctt     720
aaggcgacgt gcgtcctcaa gctgctcttg tgttaatggt ttcttttttg tgctcatcct    780
aggaatctat caccgcaagg gataaatatc taacaccgtg cgtgttgaca attttacctc    840
tggcggtgat aatggttgca tgtactaagg aggttataag tatactcaca ctggctcacc    900
ttcgggtggg cctttctgcg gatcc                                           925

<210> SEQ ID NO 24
<211> LENGTH: 135
<212> TYPE: DNA
<213> ORGANISM: Artificial Sequence
<220> FEATURE:
<223> OTHER INFORMATION: AvrII-PlambdaR03-RBS01-T7RNApol-F
      oligonucleotide

<400> SEQUENCE: 24
ctcatcctag gaatctatca ccgcaaggga taaatatcta acaccgtgcg tgttgatcat     60

```
tttacctctg gcggtgataa tggttgcatg tactaaggag gttataaatg aacacgatta    120
acatcgctaa gaacg                                                    135
```

<210> SEQ ID NO 25
<211> LENGTH: 84
<212> TYPE: DNA
<213> ORGANISM: Artificial Sequence
<220> FEATURE:
<223> OTHER INFORMATION: T7RNApol-BstZ17I-TT07-BamHI-XhoI-R
      oligonucleotide

<400> SEQUENCE: 25

```
cggccagctc gagcgcggat ccgcagaaag gcccacccga aggtgagcca gtgtgagtat    60
acttacgcga acgcgaagtc cgac                                          84
```

<210> SEQ ID NO 26
<211> LENGTH: 20
<212> TYPE: DNA
<213> ORGANISM: Artificial Sequence
<220> FEATURE:
<223> OTHER INFORMATION: malS-F oligonucleotide

<400> SEQUENCE: 26

```
gcaccaacaa cgcttcaggc                                               20
```

<210> SEQ ID NO 27
<211> LENGTH: 20
<212> TYPE: DNA
<213> ORGANISM: Artificial Sequence
<220> FEATURE:
<223> OTHER INFORMATION: Km-R oligonucleotide

<400> SEQUENCE: 27

```
tgtaggctgg agctgcttcg                                               20
```

<210> SEQ ID NO 28
<211> LENGTH: 20
<212> TYPE: DNA
<213> ORGANISM: Artificial Sequence
<220> FEATURE:
<223> OTHER INFORMATION: T7RNApol-F oligonucleotide

<400> SEQUENCE: 28

```
gctgctaagc tgctggctgc                                               20
```

<210> SEQ ID NO 29
<211> LENGTH: 19
<212> TYPE: DNA
<213> ORGANISM: Artificial Sequence
<220> FEATURE:
<223> OTHER INFORMATION: malS-R oligonucleotide

<400> SEQUENCE: 29

```
ggaaagactc atgcacagc                                                19
```

<210> SEQ ID NO 30
<211> LENGTH: 22
<212> TYPE: DNA
<213> ORGANISM: Artificial Sequence
<220> FEATURE:
<223> OTHER INFORMATION: Ome1707-DwcaM-verif-F

<400> SEQUENCE: 30

```
gccgttcaac actggctgga cg                                            22
```

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31

```
tgccattgca ggtgcatcgc                                                 20
```

<210> SEQ ID NO 32
<211> LENGTH: 914
<212> TYPE: DNA
<213> ORGANISM: Artificial Sequence
<220> FEATURE:
<223> OTHER INFORMATION: Plasmid pMA-RQ-TTadc-CI*3-PlambdaR*(-35)-
    RBS01*2

<400> SEQUENCE: 32

```
ggccgtcaag gccgcatggc gcgccttata acctccttag tacatgcaac cattatcacc     60
gccagaggta aaattgtcaa cacgcacggt gttagatatt tatcccttgc ggtgatagat    120
ttaacgtatg agcacaaaaa agaaaccatt aacacaagag cagcttgagg acgcacgtcg    180
ccttaaggca attcatgaaa aaagaaaaa tgaacttggc ttatcccagg aatctgtcgc     240
agacaagatg gggatggggc agtcaggcgt tggtgcttta tttaatggca tcaatgcatt    300
aaatgcttac aacgccgcat tgcttgcgaa aattctcaaa gttagcgttg aagaatttag    360
cccttcaatc gccagagaaa tctacgagat gtatgaagcg ttagcatgc agccgtcact    420
tagaagtgag tatgagtacc ctgttttttc tcatgttcag gcaggatgt tctcacctga    480
acttagaacc tttaccaaag gtgatgcgga gagatgggta agcacaacca aaaaagccag    540
tgattctgca ttctggcttg aggttgaagg taattccatg accgcaccaa caggctccaa    600
gccaagcttt cctgacggaa tgttaattct cgttgaccct gagcaggctg ttgagccagg    660
tgatttctgc atagccagac ttgggggtga tgagtttacc ttcaagaaac tgatcaggga    720
tagcggtcag gtgtttttac aaccactaaa cccacagtac ccaatgatcc catgcaatga    780
gagttgttcc gttgtgggga agttatcgc tagtcagtgg cctgaagaga cgtttggctg    840
ataaaaaaaa taagagttac catttaaggt aactcttatt tttagggccc ttaattaact    900
gggcctcatg ggcc                                                     914
```

<210> SEQ ID NO 33
<211> LENGTH: 914
<212> TYPE: DNA
<213> ORGANISM: Artificial Sequence
<220> FEATURE:
<223> OTHER INFORMATION: Plasmid pMA-RQ-TTadc-CI*3-PlambdaR*(-35)-
    RBS01*2

<400> SEQUENCE: 33

```
ggccgtcaag gccgcatggc gcgccttata acctccttag tacatgcaac cattatcacc     60
gccagaggta aaattgtcaa cacgcacggt gttagatatt tatcccttgc ggtgatagat    120
ttaacgtatg agcacaaaaa agaaaccatt aacacaagag cagcttgagg acgcacgtcg    180
ccttaaggca atttatgaaa aaagaaaaa tgaacttggc ttatcccagg aatctgtcgc     240
agacaagatg gggatggggc agtcaggcgt tggtgcttta tttaatggca tcaatgcatt    300
aaatgcttac aacgccgcat tggcgacaaa aattctcaaa gttagcgttg aagaatttag    360
```

```
cccttcaatc gccagagaaa tctacgagat gtatgaagcg gttagcatgc agccgtcact    420
tagaagtgag tatgagtacc ctgttttttc tcatgttcag gcaggatgt tctcacctaa     480 gcttagaacc tttaccaaag gtgatgcgga gagatgggta agcacaacca aaaaagccag    540
tgattctgca ttctggcttg aggttgaagg taattccatg accgcaccaa caggctccaa    600
gccaagcttt cctgacggaa tgttaattct cgttgaccct gagcaggctg ttgagccagg    660
tgatttctgc atagccagac ttgggggtga tgagtttacc ttcaagaaac tgatcaggga    720
tagcggtcag gtgtttttac aaccactaaa cccacagtac ccaatgatcc catgcaatga    780
gagttgttcc gttgtgggga agttatcgc tagtcagtgg cctgaagaga cgtttggctg     840
ataaaaaaaa taagagttac catttaaggt aactcttatt tttagggccc ttaattaact    900
gggcctcatg ggcc                                                      914

<210> SEQ ID NO 34
<211> LENGTH: 95
<212> TYPE: DNA
<213> ORGANISM: Artificial Sequence
<220> FEATURE:
<223> OTHER INFORMATION: Oligonucleotide

<400> SEQUENCE: 34
gcccaagctt tgtaggctgg agctgcttcg aagttcctat actttctaga gaataggaac    60
ttcggaatag gaaccggatc aattcatcgc gcgtc                               95

<210> SEQ ID NO 35
<211> LENGTH: 102
<212> TYPE: DNA
<213> ORGANISM: Artificial Sequence
<220> FEATURE:
<223> OTHER INFORMATION: Oligonucleotide

<400> SEQUENCE: 35
tcccccgggg tataccatat gaatatcctc cttagttcct attccgaagt tcctattctc    60
tagaaagtat aggaacttcg aattgtcgac aagctagctt gc                       102

<210> SEQ ID NO 36
<211> LENGTH: 39
<212> TYPE: DNA
<213> ORGANISM: Artificial Sequence
<220> FEATURE:
<223> OTHER INFORMATION: Oligonucleotide

<400> SEQUENCE: 36
cgtaggcgcc ggtaccgagt gcagatcggc tggaaggcg                           39

<210> SEQ ID NO 37
<211> LENGTH: 115
<212> TYPE: DNA
<213> ORGANISM: Artificial Sequence
<220> FEATURE:
<223> OTHER INFORMATION: Oligonucleotide

<400> SEQUENCE: 37
gcttgtatac aacagataaa acgaaaggcc cagtctttcg actgagcctt tcgttttatt    60
tgatgcattt ctgtagaatt ttacacttat agtatcatta ctgattgaga cttca         115

<210> SEQ ID NO 38
<211> LENGTH: 108
<212> TYPE: DNA
<213> ORGANISM: Artificial Sequence
```

```
<220> FEATURE:
<223> OTHER INFORMATION: Oligonucleotide

<400> SEQUENCE: 38
agactgggcc tttcgtttta tctgttgtat acaagcttta cctagggccc ttaattaaat    60
aatgaataag ggtgtttaag taaaggaaaa catcaccgtt cctggcat                108

<210> SEQ ID NO 39
<211> LENGTH: 42
<212> TYPE: DNA
<213> ORGANISM: Artificial Sequence
<220> FEATURE:
<223> OTHER INFORMATION: Oligonucleotide

<400> SEQUENCE: 39
cgtaggcgcc ggtacccagc ataatcattc accacacatc cg                       42

<210> SEQ ID NO 40
<211> LENGTH: 109
<212> TYPE: DNA
<213> ORGANISM: Artificial Sequence
<220> FEATURE:
<223> OTHER INFORMATION: Oligonucleotide

<400> SEQUENCE: 40
tcccccgggg tatactgtag gctggagctg cttcgaagtt cctatacttt ctagagaata    60
ggaacttcgg aataggaact tcatttagat gggtaccgag ctcgaattg              109

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide

<400> SEQUENCE: 41
cagaccaccc aactggcgac c                                              21

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide

<400> SEQUENCE: 42
gccattggaa tcgaccagcc                                                20

<210> SEQ ID NO 43
<211> LENGTH: 21
<212> TYPE: DNA
<213> ORGANISM: Artificial Sequence
<220> FEATURE:
<223> OTHER INFORMATION: Oligonucleotide

<400> SEQUENCE: 43
ggttgctggc gcctatatcg c                                              21

<210> SEQ ID NO 44
<211> LENGTH: 25
<212> TYPE: DNA
<213> ORGANISM: Artificial Sequence
<220> FEATURE:
<223> OTHER INFORMATION: Oligonucleotide
```

<400> SEQUENCE: 44
gcctggtgga gtttaatgat gtcgc                                           25

<210> SEQ ID NO 45
<211> LENGTH: 101
<212> TYPE: DNA
<213> ORGANISM: Artificial Sequence
<220> FEATURE:
<223> OTHER INFORMATION: Oligonucleotide

<400> SEQUENCE: 45
cccaagcttc atatgaatat cctccttagt tcctattccg aagttcctat tctctagaaa    60
gtataggaac ttcggcgcgg atgggtaccg agctcgaatt g                       101

<210> SEQ ID NO 46
<211> LENGTH: 41
<212> TYPE: DNA
<213> ORGANISM: Artificial Sequence
<220> FEATURE:
<223> OTHER INFORMATION: Oligonucleotide

<400> SEQUENCE: 46
cgtaggcgcc ggtaccgacc tcaatatcga cccagctacg c                        41

<210> SEQ ID NO 47
<211> LENGTH: 95
<212> TYPE: DNA
<213> ORGANISM: Artificial Sequence
<220> FEATURE:
<223> OTHER INFORMATION: Oligonucleotide

<400> SEQUENCE: 47
gcttgtatac aacagataaa acgaaaggcc cagtctttcg actgagcctt tcgttttatt    60
tgatgcattg aaatgctcat agggtatcgg gtcgc                                95

<210> SEQ ID NO 48
<211> LENGTH: 90
<212> TYPE: DNA
<213> ORGANISM: Artificial Sequence
<220> FEATURE:
<223> OTHER INFORMATION: Oligonucleotide

<400> SEQUENCE: 48
agactgggcc tttcgtttta tctgttgtat acaagcttaa ttaacctagg gcccgggcgg    60
atccgtgagt gatgtgaaag cctgacgtgg                                      90

<210> SEQ ID NO 49
<211> LENGTH: 42
<212> TYPE: DNA
<213> ORGANISM: Artificial Sequence
<220> FEATURE:
<223> OTHER INFORMATION: Oligonucleotide

<400> SEQUENCE: 49
cgtaggcgcc ggtacccgaa ctgcactaag taacctcttc gg                        42

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide

<400> SEQUENCE: 50

```
<210> SEQ ID NO 51
<211> LENGTH: 22
<212> TYPE: DNA
<213> ORGANISM: Artificial Sequence
<220> FEATURE:
<223> OTHER INFORMATION: Oligonucleotide

<400> SEQUENCE: 51
gccggttatc catcaggttc ac                                          22

<210> SEQ ID NO 52
<211> LENGTH: 23
<212> TYPE: DNA
<213> ORGANISM: Artificial Sequence
<220> FEATURE:
<223> OTHER INFORMATION: Oligonucleotide

<400> SEQUENCE: 52
ggtattccac gggattttc gcg                                          23

<210> SEQ ID NO 53
<211> LENGTH: 25
<212> TYPE: DNA
<213> ORGANISM: Artificial Sequence
<220> FEATURE:
<223> OTHER INFORMATION: Oligonucleotide

<400> SEQUENCE: 53
cgtcagtaat cacattgcct gttgg                                       25

<210> SEQ ID NO 54
<211> LENGTH: 118
<212> TYPE: DNA
<213> ORGANISM: Artificial Sequence
<220> FEATURE:
<223> OTHER INFORMATION: Oligonucleotide

<400> SEQUENCE: 54
tgccggcacg gcgccaagtt aaccctaggt tatctctggc ggtgttgaca taaataccac    60
tggcggttat actgagcaca tcaactaagg aggttataaa tgagagtgtt gaagttcg     118

<210> SEQ ID NO 55
<211> LENGTH: 19
<212> TYPE: DNA
<213> ORGANISM: Artificial Sequence
<220> FEATURE:
<223> OTHER INFORMATION: Oligonucleotide

<400> SEQUENCE: 55
ccgggtcagc ggcgtaggc                                              19
```